US 6,617,425 B1

(12) United States Patent
Seebach

(10) Patent No.: US 6,617,425 B1
(45) Date of Patent: Sep. 9, 2003

(54) PEPTIDES

(75) Inventor: Dieter Seebach, Zurich (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/202,098

(22) PCT Filed: Jun. 12, 1997

(86) PCT No.: PCT/EP97/03077

§ 371 (c)(1),
(2), (4) Date: Dec. 9, 1998

(87) PCT Pub. No.: WO97/47593

PCT Pub. Date: Dec. 18, 1997

(30) Foreign Application Priority Data

Oct. 15, 1996 (GB) ............................. 9621496
Jun. 13, 1996 (GB) ............................. 9612402

(51) Int. Cl.$^7$ ............................. C07K 7/00
(52) U.S. Cl. .................. 530/329; 530/327; 530/328; 530/330; 530/317; 514/15; 514/16; 514/17; 514/18
(58) Field of Search ............ 519/16–19; 530/329, 530/330, 331

(56) References Cited

U.S. PATENT DOCUMENTS

| | | | | |
|---|---|---|---|---|
| 2,749,331 A | * | 6/1956 | Breslow | 260/89.7 |
| 5,693,751 A | * | 12/1997 | Sakurai | 530/322 |
| 5,756,502 A | * | 5/1998 | Padia | 514/248 |
| 5,962,502 A | * | 10/1999 | Makovec | 514/415 |

OTHER PUBLICATIONS

Dutta, Journal of Peptide Science 6, 321, 2000.*
Albericio et al., Chemical Abstracts No. 225200, vol. 104, No. 25 (1986).
Drey et al., Chemical Abstract No. 66810b, vol. 79, No. 11 (1973).
Drey et al., Chemical Abstracts #206530, vol. 83, No. 25, (1975).
Drey et al., J. Chem. Soc., Perkin Trans. vol. 1, pp. 1587–1592 (1982).
Hintermann et al., Synlett, vol. 5, pp. 437–438 (1997).
J. Podlech et al., Angewandte Chemie, International Edition, vol. 34, No. 4, pp. 471–472 (1995).
Lowbridge et al., J. Chem. Soc., Perkin trans 1, pp. 155–156, (1986).
Rothe et al., Angew. Chem. vol. 91 No. 1, pp. 79–80 (1979).
Seebach et al., Helv. Chim. Acta, vol. 80(1), pp. 173–182 (1997).
Seebach et al. Chem. Commun., β–Peptides: a surprise at every turn, pp. 2015–2022 Laboratorium Für Organische Chemie, ETH–Zentrum, Universitätsstrasse 16I, CH 8092, Zü (1997)rich, Switzerland.
Seebach et al., Helv. Chim. Acta, vol. 79 (8), pp. 2043–2066 (1996).
Seebach et al., Helv. Chim. Acta, vol. 79(4) pp. 913–941 (1996).
White et al., J. Chem. Soc., Perkin Trans. vol. 2 (2), pp. 239–243 (1982).
Hanabuso et al., Angew. Makromol. Chem. (1980) vol. 84, pp. 97–104 (1980), Functional Monomers and Polymers, 64*.
Albericio et al., Afinidad Sep.–Oct., 1985, pp. 491–496, Properties of bromomethyl–NBB–resin: Application to the synthesis of protected peptides and oligoamides, as demonstrated by synthesis of Boc–(β–Ala)$_4$–OH.
Drey et al., Organic Mass Spectrometry, vol. 7, pp. 779–780 (1973), The Mass Spectra of Cyclo–Tripeptides of B–Alanine and 3–Amino–3Methyl Butanoic Acid.
Drey et al., Pept., Proc. Eur. Pet. Symp. 13$^{th}$ (1975) Meeting Date 1974, pp. 419–422, The Synthesis of Peptides Derived from α–Amino–Acids.

* cited by examiner

Primary Examiner—Christopher S. F. Low
Assistant Examiner—David Lukton
(74) Attorney, Agent, or Firm—Gregory D. Ferraro

(57) ABSTRACT

The invention provides novel β-peptides comprising 2 or more different β-amino acid residues, preferably compounds of formula I $$\underset{R_2}{\overset{R_1}{N}}{\overset{*}{-}}\underset{R}{\overset{R_3}{\underset{*}{C}}}{-}\overset{O}{\underset{\|}{C}}{-}\left[\underset{R}{\overset{H}{\underset{*}{N}}}{-}\underset{R}{\overset{R_3}{\underset{*}{C}}}{-}\overset{O}{\underset{\|}{C}}\right]_n{-}OX \qquad \text{I}$$

wherein the R residues, X and n are as defined. Compounds of the invention having as few as 5 or 6 β-amino acid residues exhibit stable structures in solution and the compounds generally exhibit good resistance to proteolytic degradation. The compounds of the invention provide a valuable new source of structural diversity for synthesis of biologically active compounds, e.g. for pharmaceutical uses.

8 Claims, 6 Drawing Sheets

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Peptide of
      Beta-amino acids

<400> SEQUENCE: 1

Val Ala Leu Val Ala Leu
 1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Peptide of
      Beta-amino acids

<400> SEQUENCE: 2

Ala Val Ala Leu
 1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Peptide of
      Beta-amino acids

<400> SEQUENCE: 3

Gly Val Ala Leu
 1

<210> SEQ ID NO 4
```

-continued

```
<211> LENGTH: 7
<212> TYPE: PRT
<213> ORGANISM: Artificial Sequence
<220> FEATURE:
<223> OTHER INFORMATION: Description of Artificial Sequence: Peptide of
      Beta-amino acids

<400> SEQUENCE: 4

Val Ala Leu Gly Val Ala Leu
 1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Peptide of
      Beta-amino acids

<400> SEQUENCE: 5

Val Ala Leu Ala Val Ala Leu
 1               5
```

PEPTIDES

Many naturally occurring, biologically active compounds are proteins or peptides based upon α-amino acids (i.e. sequences of α-amino acids in which the α-carboxyl group of one amino acid is joined by an amide bond to the α-amino group of the adjacent amino acid). In recent years an approach to the discovery of new pharmaceutically active drugs has been to synthesise libraries of peptides and then to assay for compounds within the library which have a desired activity, such as a desired binding activity. However, α-amino acid peptides are not altogether satisfactory for pharmaceutical uses, in particular because they are often poorly absorbed and subject to proteolytic degradation in vivo.

We have now synthesised new peptides based on β-amino acids and have found that these peptides have unexpected and desirable properties.

Accordingly the present invention provides a β-peptide comprising 2 or more different β-amino acid residues.

For the purposes of the present description a β-peptide comprises a sequence of 2 or more β-amino acid residues in which the α-carboxyl group of one amino acid is joined by an amide bond to the β-amino group of the adjacent amino acid. The β-peptides of the invention may comprise any number of amino acid residues, though conveniently comprise from 2 to 11, preferably from 4 to 7, especially 5 or 6, β-amino acid residues.

DETAILED DESCRIPTION OF THE PREFERRED EMBODIMENTS

The β-amino acid residues of the β-peptides of the invention are characteristically β-amino-n-propionic acid derivatives, typically further substituted at the α- and/or β-carbon atoms and may be further substituted, e.g. at the N-terminal amino nitrogen atom. The α-, β- and and amino substituents may include substituents containing from 1 to 43 carbon atoms optionally interrupted by up to 4 hetero atoms, selected from O, N or S, optionally containing a carbonyl (i.e. —C(O)—) group, and optionally further substituted by up to 6 substituents selected from halo, $NO_2$, —OH, $C_{1-4}$alkyl, —SH, —$SO_3$, —$NH_2$, $C_{1-4}$acyl, $C_{1-4}$acyloxy, $C_{1-4}$alkylamino, $C_{1-4}$dialkylamino, trihalomethyl, —CN, $C_{1-4}$alkylthio, $C_{1-4}$alkylsulfinyl, or $C_{1-4}$alkylsulfonyl. Conveniently, the α-, β- and amino substituents may include any of those substituents defined below as the "R" substituents of formula I. For example, the α- and β-substituents may be selected from the group comprising the substituents which are present on the α-carbon atoms of α-amino acids, e.g. —H, —$CH_3$, —CH($CH_3$)$_2$, —$CH_2$—CH($CH_3$)$_2$, —CH($CH_3$)$CH_2CH_3$, —$CH_2$-phenyl, $CH_2$-pOH-phenyl, —$CH_2$-indole, —$CH_2$—SH, —$CH_2$—$CH_2$—S—$CH_3$, —$CH_2$OH, —CHOH—$CH_3$, —$CH_2$—$CH_2$—$CH_2$—$CH_2$—$NH_2$, —$CH_2$—$CH_2$—$CH_2$—NH—C(NH)$NH_2$, —$CH_2$-imidazole, —$CH_2$—COOH, —$CH_2$—$CH_2$-COOH, —$CH_2$—$CONH_2$, —$CH_2$—$CH_2$-$CONH_2$ or together with an adjacent —NH group forms a proline amino acid residue.

The β-peptides of the invention preferably comprise only β-amino acid residues. However, the invention includes β-peptides, for instance longer β-peptides, e.g. comprising 7 or more acid residues, which contain one or a few, e.g. 1 or 2, acid residues which are not β-amino acids, e.g. α- or γ-amino acids, or an α-, β- or γ-hydroxycarboxlic acids. For example, a non-β-amino acid may be present in the β-peptide at a junction or transition region between two sequences of β-amino acid residues.

Characteristically substitutents present on the α- and/or β-carbon atoms of the β-amino acid residues are in the radial orientation with respect to the peptide chain.

Preferably the present invention provides a compound of formula I

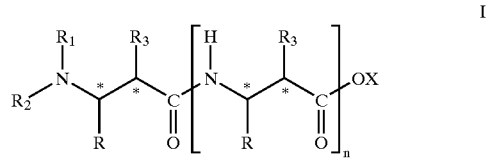

wherein each R is H, —$R_5$, —$OR_5$, —$C(O)R_5$, —$R_5C(O)R_6$, —$C(O)OR_5$, —$R_5C(O)OR_6$, —$R_5OC(O)R_6$, —$R_5OC(O)OR_6$, —$R_5NR_6C(O)R_7$, —$R_5C(O)NR_6R_7$, —$C(O)NR_6R_7$, —$R_5OC(O)NR_6R_7$, —$R_5NR_6C(O)NR_7R_8$, —$R_5NR_6C(O)OR_7$, —$R_5$—O—$R_6$, —$R_5$—$NR_6R_7$, —$R_5$—S—$R_6$, —$R_5SO_mR_6$, —$R_5OR_6$—O—$R_7$, —$R_5NR_6R_7$—O—$R_8$, —$R_5SO_mR_6$—O—$R_7$, —$C(O)R_5$—O—$R_6$, —$C(O)OR_5$—O—$R_6$, —$R_5C(O)R_6$—O—$R_7$, —$R_5C(O)OR_6$—O—$R_7$, —$R_5OC(O)R_6$—O—$R_7$, —$R_5OC(O)OR_6$—O—$R_7$, —$R_5NR_6C(O)R_7$—O—$R_8$, —$C(O)NR_5R_6$—O—$R_7$, —$R_5C(O)NR_6R_7$—O—$R_8$, —$R_5OC(O)NR_6R_7$—O—$R_8$, —$R_5NR_6C(O)NR_7R_8$—O—$R_9$, —$R_5NR_6C(O)OR_7$—O—$R_8$, —$R_5OR_6$—S—$R_7$, —$R_5NR_6R_7$—S—$R_8$, —$R_5SO_mR_6$—S—$R_7$, —$C(O)R_5$—S—$R_6$, —$C(O)OR_5$—S—$R_6$, —$R_5C(O)R_6$—S—$R_7$, —$R_5C(O)OR_6$—S—$R_7$, —$R_5OC(O)R_6$—S—$R_7$, —$R_5OC(O)OR_6$—S—$R_7$, —$R_5NR_6C(O)R_7$—S—$R_8$, —$C(O)NR_5R_6$—S—$R_7$, —$R_5C(O)NR_6R_7$—S—$R_8$, —$R_5OC(O)NR_6R_7$—S—$R_8$, —$R_5NR_6C(O)NR_7R_8$—S—$R_9$, —$R_5NR_6C(O)OR_7$—S—$R_8$, —$R_5OR_6$—$NR_7R_8$, —$R_5NR_6R_7$—$NR_8R_9$, —$R_5SO_mR_6$—$NR_7R_8$, —$C(O)R_5$—$NR_6R_8$, —$C(O)OR_5$—$NR_6R_8$, —$R_5C(O)R_6$—$NR_7R_8$, —$R_5C(O)OR_6$—$NR_7R_8$, —$R_5OC(O)R_6$—$NR_7R_8$, —$R_5OC(O)OR_6$—$NR_7R_8$, —$R_5NR_6C(O)R_7$—$NR_8R_9$, —$C(O)NR_5R_6$—$NR_7R_8$, —$R_5C(O)NR_6R_7$—$NR_8R_9$, —$R_5OC(O)NR_6R_7$—$NR_8R_9$, —$R_5NR_6C(O)NR_7R_8$—$NHR_9$ or —$R_5NR_6C(O)OR_7$—$NR_8R_9$, where $R_5$, $R_6$, $R_7$, $R_8$ and $R_9$ are each independently $C_{1-10}$alkyl, $C_{1-10}$alkenyl, $C_{1-10}$alkynyl, $C_{6-10}$aryl, $C_{6-14}$aralkyl, $C_{6-14}$aralkenyl or $C_{6-14}$aralkynyl and m is 1,2,3 or 4; and where $R_5$ $R_6$, $R_7$, $R_8$ and $R_9$ are each unsubstituted or substituted with up to 6 substituents selected from halo, $NO_2$, —OH, $C_{1-4}$alkyl, —SH, —$SO_3$, —$NH_2$, $C_{1-4}$acyl, $C_{1-4}$acyloxy, $C_{1-4}$alkylamino, $C_{1-4}$dialkylamino, trihalomethyl, —CN, $C_{1-4}$alkylthio, $C_{1-4}$alkylsulfinyl, or $C_{1-4}$alkylsulfonyl, provided that all the R substituents are not identical, or R forms a cyclic structure, e.g. a carbocyclic or heterocyclic ring, with itself, with $R_3$ or with the carbonyl group attached to the immediately adjacent nitrogen atom;

$R_1$ and $R_2$, which may be the same or different, are H, an N-protecting group or as defined above for R, or $R_1$ and $R_2$ are linked together in a 3 to 7 membered heterocyclic ring structure, or either $R_1$ or $R_2$ together with OX signify an amide bond;

each $R_3$, which may be the same or different, is as defined above for R, or $R_3$ forms a cyclic structure, e.g. a carbocyclic or heterocyclic ring, with itself, with R or with the nitrogen atom of its β-amino acid residue, provided that R and $R_3$ are not both H;

X is H, an O-protecting group or as defined above for R, except that X is not —$OR_5$, or OX together with $R_1$ or $R_2$ signify an amide bond;

n is 1,2,3,4,5,6,7,8,9, or 10.

The β-peptides of the invention, and in particular the compounds of formula I, are hereinafter referred to as the compounds of the invention.

Characteristically when R and $R_3$ are not H, R and $R_3$ are in the radial orientation with respect to the peptide chain.

Typically when R or $R_3$ form a cyclic structure, the cyclic structure is a 3 to 7 membered cyclic structure.

Preferably n is 4, 5, 6 or 7 or more preferably n is 5 or 6.

Thus in preferred embodiments the invention provides a compound of formula II or a compound of formula III

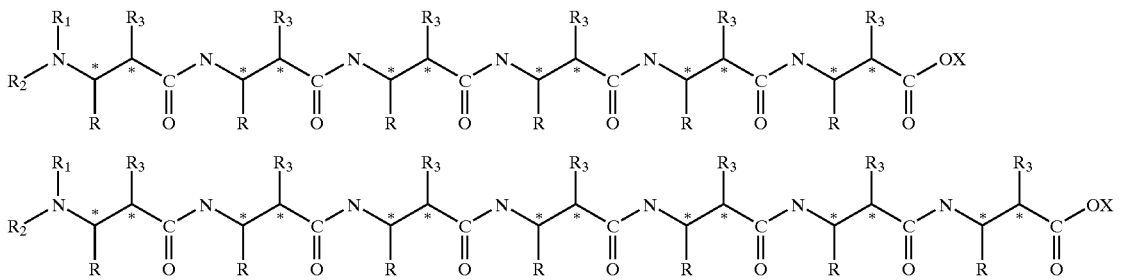

wherein R, $R_1$, $R_2$, $R_3$ and X are as defined above.

When $R_1$ and $R_2$ are linked together in a ring structure the structure is optionally substituted as for $R_5$ etc. above and may be fused with one or more rings such as phenyl rings. For example the $R_1$ and $R_2$ ring system may be a piperidine or pyridine ring system.

When either $R_1$ or $R_2$ together with OX signify an amide bond, i.e. when the compounds of formula I are cyclic compounds, n is preferably at least 2.

In the present description unless otherwise indicated terms such as "compounds of the invention" embrace the compounds in salt form as well as in free base form and also when the compounds are attached to a solid phase. Where a basic substituent such as an amine substituent is present, the salt form may be a double acid addition salt, for example a dihydrochloride.

The term halogen includes F, Cl, Br and I, preferably F and Cl.

Suitable N-protecting groups as $R_1$ or $R_2$ include groups of formula $H(CH_2CH_2O)_p$— where p=3–30; $R_{10}CO$—; $R_{11}OCO$— or $R_{12}SO_2$—, in which $R_{10}$ is $C_{1-4}$ alkyl or $H(CH_2$—O—$CH_2)_p$ wherein p is defined as above;

$R_{11}$ is $C_{1-6}$ alkyl, phenyl, benzyl or naphthyl; and $R_{12}$ is phenyl, naphthyl, or $C_{1-4}$ alkylphenyl;

of which $R_{11}OCO$— is particularly preferred, especially when $R_{11}$ is tert. butyl (i.e. Boc as the protecting group), or when $R_{11}$ is benzyl (i.e. the protecting group customarily designated as Z).

Suitable O-protecting groups as X include are alkyl, e.g. $C_{1-4}$ alkyl, groups or aromatic groups, e.g. benzyl, including substituted phenyl groups such pentafluorophenyl.

In a particular embodiment the compounds of formula I are peptides of β-amino acids which are unsubstituted at the α-carbon atom, i.e. compounds of formula IV

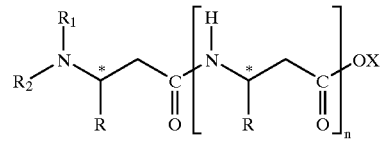

wherein R, $R_1$, $R_2$, X and n are as defined above.

β-amino acids which are unsubstituted at the α-carbon atom and the corresponding peptides of formula IV are conveniently referred to as $β^3$ amino acids and $β^3$ peptides respectively.

In a further particular embodiment the compounds of formula I are peptides of β-amino acids which are unsubstituted, apart from amino substituted, at the β-carbon atom, i.e. compounds of formula V

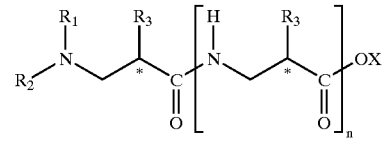

wherein $R_1$, $R_2$, $R_3$, X and n are as defined above.

β-amino acids which are unsubstituted, apart from the amino substitituent, at the β-carbon atom and the corresponding peptides of formula V are conveniently referred to as $β^2$ amino acids and $β^2$ peptides respectively.

In further particular embodiments the compounds of the invention comprise a mixture of $β^2$- and $β^3$-amino acids; for instance, as alternating $β^2$- and $β^3$-amino acids or as discrete stretches of $β^2$-amino acids linked to discrete stretches of $β^3$-amino acids.

The substituents R, $R_1$, $R_2$, $R_3$ and X have many possible significations as indicated above. Conveniently, however, in particular embodiments the substituents R, $R_1$, $R_2$, $R_3$ and X may be selected from the group comprising the substituents which are present on the α-carbon atoms of α-amino acids, e.g. —H, —$CH_3$, —$CH(CH_3)_2$, —$CH_2$—$CH(CH_3)_2$, —CH($CH_3$)$CH_2CH_3$, —$CH_2$phenyl, $CH_2$—pOH-phenyl, —$CH_2$-indole, —$CH_2$—SH, —$CH_2$—$CH_2$—S—$CH_3$, —$CH_2OH$, —CHOH—$CH_3$, —$CH_2$—$CH_2$—$CH_2$—$CH_2$—$NH_2$, —$CH_2$—$CH_2$—$CH_2$—NH—C(NH)$NH_2$, —$CH_2$-imidazole, —$CH_2$—COOH, —$CH_2$—$CH_2$—COOH, —$CH_2$—$CONH_2$, —$CH_2$—$CH_2$—$CONH_2$ or together with an adjacent —NH group forms a proline amino acid residue.

In accordance with the present invention it has been found that the compounds of the invention have desirable properties. For example, compounds of formula I in which n is 5 or 6 are able to form stable helix structures in solution, in contrast to α-peptides for which distinct secondary structures are observed in solution only when the peptide comprises at least 15 to 20 amino acid residues. Thus it has been found that representative compounds of formula I comprising L-β-amino acids form compact, left-handed or (M) $3_1$ helices of 5 Å pitch. Representative compounds of formula I comprising D-β-amino acids form corresponding compact, right-handed helices. The corresponding helices formed by α-peptides of L-amino acids are right-handed $3.6_{13}$ α-helices with a pitch of 5.6 Å. Other structures of the compounds of the invention are discussed hereinafter and in the references referred to hereinafter.

In view of their structure and in preferred embodiments β-peptides of the invention, especially β-hexapeptides, may be used as β-turn mimetics.

Generally also the compounds of the invention have much greater stability to the action of peptidases, such as pepsin, than α-peptides. As such the compounds of formula may conveniently exhibit correspondingly longer half lives, e.g. serum half lives, in vivo than than α-peptides.

In formula I above the carbon atoms marked with an asterisk (*) may be optically active centres, i.e. when R and $R_3$ are not H, and may be in the R or the S configuration. Thus the invention includes the compounds of the invention in pure isomeric form, e.g. consisting of at least 90%, preferably at least 95% of a single isomeric form, as well as mixtures of these forms. Thus the compounds of the invention may be in the form of individual enantiomers or may be in the form of racemates or diastereoisomeric mixtures or any other mixture of the possible isomers (e.g. as derived from a racemic building block).

The compounds of the invention may be prepared by synthetic chemical procedures, including procedures similar to those which may be used for the synthesis of α-amino acid peptides. Such procedures include both solution and solid phase procedures, e.g. using both Boc and Fmoc methodologies. Thus the compounds of formula I may be prepared by successive amide bond forming procedures in which amide bonds are formed between the β-amino group of a first β-amino acid residue or a precursor thereof and the α-carboxyl group of a second β-amino acid residue or a precursor thereof. The amide bond forming step may be repeated as many times, and with specific β-amino acid residues or precursors thereof, as required to give the desired β-peptide. Also β-peptides comprising 2, 3 or more β-amino acid residues may be joined together to yield larger β-peptides. Cyclic compounds may be prepared by forming peptide bonds between the N-terminal and C-terminal ends of a previously synthesised linear β-peptide.

β-amino acids may be produced enantioselectively from corresponding α-amino acids; for instance, by Arndt-Eisert homologation of N-protected α-amino acids. Conveniently such homologation may be followed by coupling of the reactive diazo ketone intermediate of the Wolff rearrangement with a β-amino acid residue.

Thus the invention includes a process for the preparation of a compound of formula I comprising Arndt-Eisert homologation of an N-protected α-amino acid of formula VI

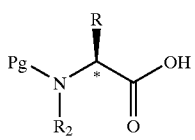

VI wherein Pg, is an amine protecting group and R and $R_2$ are as defined above, by reaction with diazomethane, e.g. in the presence of triethylamine/ethylchloroformate, to yield a diazo ketone intermediate of formula VII

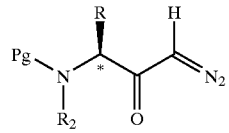

VII wherein Pg, and R and $R_3$ are as defined above.

The invention also includes a process for the preparation of a compound of formula I comprising coupling of a diazo ketone of formula VII

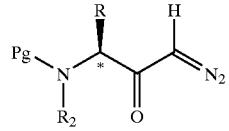

VII with a β-amino acid of formula VIII

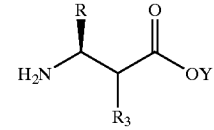

VIII wherein R and $R_3$ are as defined above and Y is an O-protecting group, or with a β-amino acid or β-peptide residue of formula IX

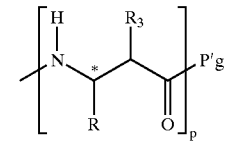

IX wherein R and $R_3$, are as defined above, P'g is an O-protecting group and p is 1, 2, 3, 4, 5, 6, 7, 8 or 9.

Any suitable reaction conditions or procedure may be used for the coupling reaction between the compounds of formulae VIII and IX. For example, the coupling reaction may be carried out in the presence of a silver catalyst, e.g. Ag benzoate in $Et_3N$, with cooling, e.g. at a temperature of 0° C. to −40° C., in the dark under an inert atmosphere. Alternatively, for example, the coupling reaction may be catalysed by light, e.g. irradiation of the reaction mixture with a low pressure mercury lamp.

The compounds of formulae of the invention may be used to establish discrete compound collections or libraries of compounds for use in screening for compounds having desirable activities, in particular biological activities indicative of particular pharmaceutical uses.

Thus the invention also includes discrete compound collections (typically comprising from 2 to about 1000 compounds) and libraries of compounds (typically comprising from 20 to 100 compounds up to many thousands of compounds, e.g. 100,000 compounds or more) comprising pluralities of the compounds of the invention.

As will be appreciated the particular identity of the substituents R, $R_1$, $R_2$, $R_3$ and X depends upon the choice of building blocks and reaction steps used for synthesis of the compounds of formula I. The substituents R, $R_1$, $R_2$, $R_3$ and X may be chosen as desired to provide groups of related compounds having particular structural themes or to provide unrelated, structurally diverse compounds.

Compounds having desired biological activities may be identified using appropriate screening assays. For example the following screening assays may be used to screen for particular biological activities indicative of corresponding pharmaceutical uses.

Antiinflammatory and immunosuppressive activities of compounds of formula I are determined by means of the following and similar assays: the IL-1β secretion inhibition, LPS fever, cytokine release from THP-1 cells, and functional IL-1 antagonist assays and the assay of carrageenan induced paw edema in the rat (as described in EP 0606044 and EP 0618223); the macrophilin binding, Mixed Lymphocyte Reaction (MLR), IL-6 mediated proliferation, localised graft-versus-host (GvH) reaction, kidney allograft reaction in the rat, experimentally induced allergic encephalomyelitis (EAE) in the rat, Freund's adjuvant arthritis, FKBP binding, steroid potentiation and Mip and Mip-like factor inhibition assays (as described in WO 94/09010, EP 0296123 and EP 0296122).

Central Nervous System (CNS) activity of compounds of formula I is determined by means of the following and similar assays: serotonin ID (5HT 10) receptor agonist assays including the method of Weber et al.(Schmiedeberg's Arch. Pharmacol. 337, 595–601 (1988)) (and as described in EP 0641787)); $5HT_3$ receptor agonist assays (as described in GB 2240476 and EP 0189002); assays for activity in treatment of psychotic disorders and Parkinson's Disease, such as the apomorphine induced gnawing in the rat assay and dopamine receptor (D1 and D2) binding assays (as described in GB 20206115 B); assays for dopamine receptor antagonist activity (in relation to schizophrenia and related diseases, as described in EP 0483063 and EP 0544240); assays for activity in relation to senile dementia and Alzheimer's Disease (as described in EP 0534904); assays for activity in relation to cerebral ischaemia (as described in EP 0433239), and assays in relation to gastrointestinal motility such as the peristaltic reflex in isolated guinea pig ileum and assays of antiserotoninergic effects (specifically at the $5-HT_4$ receptors) (as described in EP 0505322)

Activity of the compounds of formula I in relation to bone and calcium metabolism is determined by assays as or similar to those described in WO 94/02510, GB 2218102B and WO 89/09786.

Activity of the compounds of formula I in relation to asthma and other allergic and inflammatory conditions is determined by the following assay procedures: the PDE isoenzyme inhibition, inhibition of eosinophil activation by formyl Met Leu Phe (f MLP), inhibition of TNFα secretion, inhibition of SRS-A production, bacterial endotoxin (LPS) induced lethality in the guinea pig, arachidonic acid induced irritant dermatitis in the mouse, relaxation of the human bronchus, suppression of SRS-A induced bronchoconstriction, suppression of bombesin induced bronchoconstriction, suppression of methacholine (MeCH) induced bronchoconstriction in the rhesus monkey and suppression of airways hyperactivity in the guinea pig assays (as described in European patent application No. 94810628.1 [EP 0664289], WO 94/12493 and GB 2213482).

Serine protease, e.g. Thrombin, inhibition activity of the compounds of formula I is determined using assays such as those described in WO 94/20526. Glycoprotein IIb/IIIa antagonist, activity of the compounds of formula I is determined using the assay procedures described by Cook et al. (Thrombosis and Haemostasis, 70(3), 531–539 (1993) and Thrombosis and Haemostasis, 70(5), 838–847 (1993)) Müller et al. (J. Biol. Chem., Vol. 268, No. 9, 6800–6808 (1993)).

Anticancer activity of the compounds of formula I is determined by the anti tumour activity assay as described in EP 0296122 or by trial procedures, for instance as described in GB 2239178. Multidrug resistance (MDR) reversing activity is determined by the assays described in EP 0296122.

The relevant teachings of the patent documents and other publications referred to above is incorporated herein by reference. Compounds of formula I which have appropriate levels of activity in these assays are useful as pharmaceuticals in relation to the corresponding therapies or disease states.

Thus the invention includes compounds of formula I for use as pharmaceuticals and the use of a compound of formula I for the manufacture of a medicament for the. treatment of any disease associated with any of the assays hereinbefore described. The invention also includes the use of a compound of formula I as a pharmaceutical, and pharmaceutical compositions comprising an effective amount of a compound of formula I together with a pharmaceutically acceptable diluent or carrier.

Figure 1A:
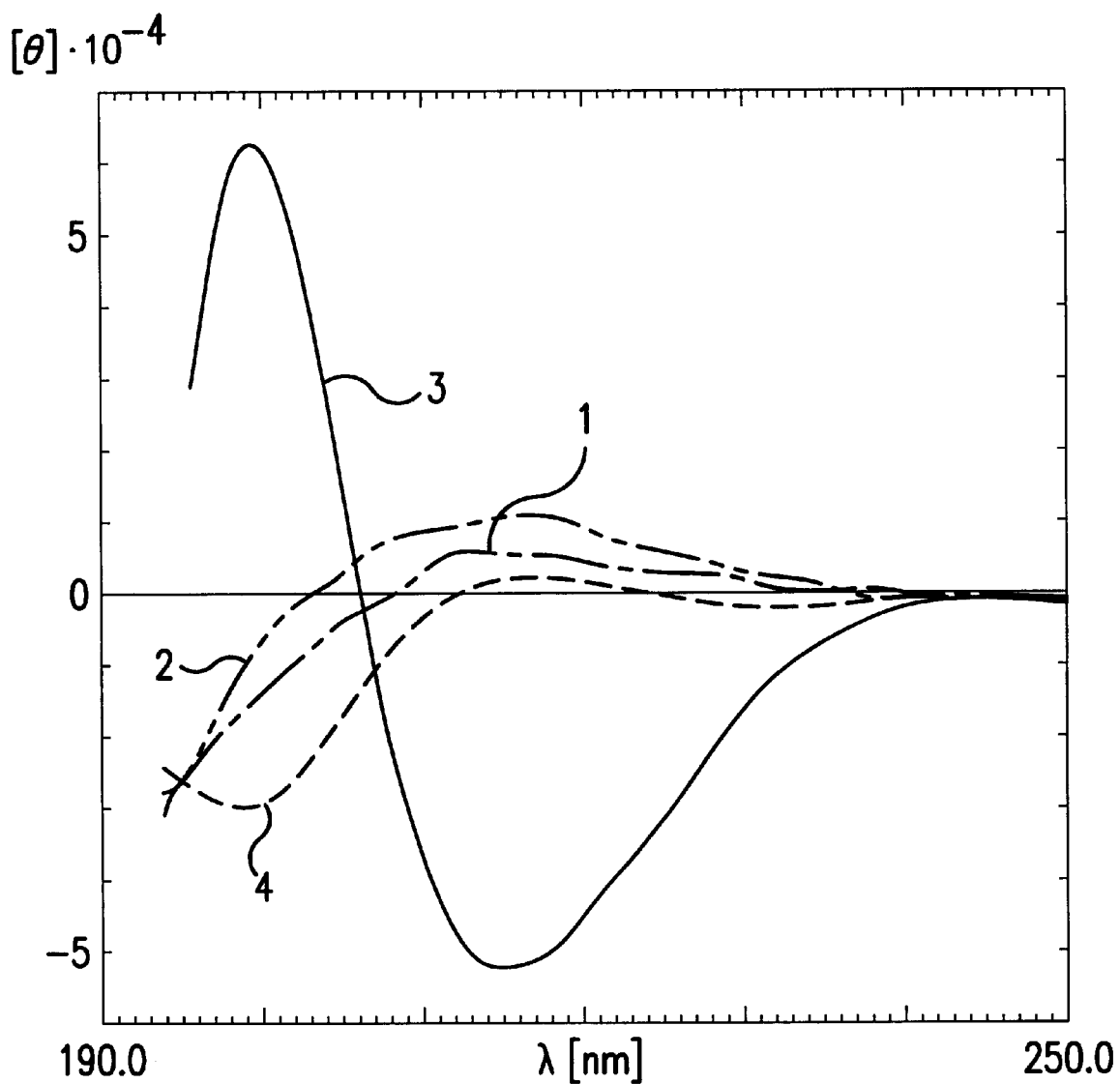
FIG. 1a is a CD spectra overlay of 1. Boc-b-HAla-b-HLeu-OMe, 2. Boc-b-HVal-b-HAla-b-HLeu-OMe, 3. H-(b-HVal-b-HAla-b-HLeu)$_2$-OMe SEQ ID NO:1 and 4. the a-hexapeptide TFA.H-Val-Ala-Leu-Val-Ala-Leu-OMe in MeOH at 0.2 mM concentration.

The synthesis and analysis of compounds of formula I is described in detail in recent publications by the inventor and co-workers, including the following 1. Seebach et al. Helvetica Chimica Acta (1996), Vol. 79, pages 913–941;
2. Seebach et al. Helvetica Chimica Acta (1996), Vol 79, pages 2043–2066;
3. T. Hintermann and D. Seebach, Synlett (1997), pages 437–438;
4. Seebach et al. Helvetica Chimica Acta (1997), Vol. 80, pages 173–182.

Thus the synthesis, analysis and properties of the following compounds of formula I are descibed in detail in publication No. 1 above:

1 i) Methyl (3S)-3-(tert-Butoxycarbonylamino)-5-methylhexanoate;

1 ii) Methyl-[(3S)-3-(tert-butoxycarbonylno)-butanoyl]-(3S)-3-amino-5-methylhexanoate (Boc-β-HAla-β-HLeu-OMe);

1 iii) Methyl-[(3S)-3-(tert-butoxycarbonylamino)-4-methylpentanoyl)-(3S)-3-aminobutanoyl]-(3S)-3-amino-5-methyl-hexanoate (Boc-β-HVal-β-HAla-β-HLeu-OMe);

1 iv) [(3S)-3-(tert-butoxycarbonylamino)-4-methylpentanoyl)-(3S)-3-aminobutanoyl](3S)-3-amino-5-methylhexanoic acid (Boc-β-HVal-β-HAla-β-HLeu-OH);

1 v) N-(tert-Butoxycarbonyl-β-homo-valine-β-homo-alanine-β-homo-leucine-β-homo-valine-β-homo-alanine-,-homo-leucine-methylester (Boc-(β-HVal-βHAla-β-HLeu)$_2$-OMe) SEQ ID NO:1;

1 vi) β-Homo-valine-β-homo-alanine-β-homo-leucine-β-homo-valine-β-homo-alanine-β-homo-leucine-methylester-trifluoroacetate (H-(β-HVal-β-HAla-β-HLeu)$_2$-OMe TFA) SEQ ID NO:1;

1 vii) N-(tert-Butoxycarbonyl)β-homo-valine-β-homo-alanine-β-homo-leucine-β-homo-valine-β-β-homo-alanine-β-homo-leucine (Boc-(β-HVal-β-HAla-β-HLeu)$_2$-OH) SEQ ID NO:1;

1 viii) β-Homo-valine-β-homo-alanine-β-homo-leucine-β-homo-valine-β-homo-alanine-β-homo-leucine-trifluoroacetete (H-(β-HVal-β-HAla-β-HLeu)$_2$-OH-TFA) SEQ ID NO:1;

1 ix) Pentafluorophenyl[(3S)-3-(tert-butoxycarbonylaminol-4-methylpentanoyl)-(3S)-3-aminobutanoyl]-(3S)-3-amino-5-methyl-hexanoate (Boc-β-HVal-β-HAla-β-HLeu-OPFP);

1 x) Cyclo(-β-HVal-β-HAla-β-HLeu);

1 xi) N-(tert-Butoxycarbony)-β-homo-valine-β-homo-alanine-β-homo-leucine-β-homo-valine-β-homo-alanine-β-homo-leucine-pentafluorophenylester(Boc(β-HVal-β-HAla-β-HLeu)$_2$-OPFP) SEQ ID NO:1;

1 xii) Cyclo(-β-HVal-β-HAla-β-HLeu-β-HVal-β-HAla-β-HLeu-) SEQ ID NO:1;

Thus the synthesis, analysis and properties of the additional following compounds of formula I are described in detail in publication No. 2 above:

2 i) Methyl-N-{(tert.-butoxy)carbonyl}-(S)-alanyl-(R)-β-homoalanyl-(S)-β-homoalanyl-(S)-β-homoleucinate (Boc-Ala-β-HVal-β-HAla-β-HLeu-OMe) SEQ ID NO:2;

2 ii) Methyl-[2-{(tert-butoxy)carbonylamino}-2-methylpropanoyl]-(R)-β-homovalyl-(S)-β-homoalanyl-(S)-,β-homoleucinate (Boc-Aib-β-HVal-β-HAla-β-HLeu-OMe);

2 iii) Methyl-[3-{(tert-butoxy)carbonylamino}-propanoyl]-(R)-β-homovalyl-(S)-βhomoalanyl-(S)-β-homoleucinate (Boc-βHGly-β-HVal-β-HAla-β-HLeu-OMe) SEQ ID NO:3;

2 iv) Methyl-N-{(tert-butoxy)carbonyl}-(S)-β-homoalanyl-(R)-β-homovalyl-(S)-β-homoalanyl-(S)-β-homoleucinate (Boc-βHAla-β-HVal-β-HAla-β-HLeu-OMe) SEQ ID NO:2;

2 v) Methyl-N-{(tert-butoxy)carbonyl}-(R)-β-homoalanyl-(R)-β-homovalyl-(S)-β-homoalanyl-(S)-β-homoleucinate (Boc-(R)-βHAla-β-HVal-β-HAla-β-HLeu-OMe) SEQ ID NO:2;

2 vi) Methyl-[3-{(tert-butoxy)carbonylamino}-3-methylbutanoyl]-(R)-β-homoalanyl-(R)-β-homovalyl-(S)-β-homoalanyl-(S)-β-homoleucinate (Boc-βHAib-β-HVal-β-HAla-β-HLeu-OMe)

2 vii) Methyl-N-{(tert-butoxy)carbonyl}-(2S,2R)-2-methyl-β-homoalanyl-(R)-β-homovalyl-(S)-β-homoalanyl-(S)-β-homoleucinate (Boc-(S,S)-β-HAla(αMe)-β-HVal-β-HAla-β-HLeu-OMe) SEQ ID NO:2;

2 viii) Methyl-N-{(tert-butoxy)carbonyl}-(2R,3S)-2-methyl-β-homoalanyl-(R)-β-homovalyl-(S)-β-homoalanyl-(S)-β-homoleucinate (Boc-(R,S)-β-HAla(αMe)-β-HVal-β-HAla-β-HLeu-OMe) SEQ ID NO:2;

2 ix) Methyl-N-{(tert-butoxy)carbonyl}-(S)-N-methyl-β-homoalanyl-(R)-β-homovalyl-(S)-β-homoalanyl-(S)-β-homoleucinate (Boc(Me)-β-HAla-β-HVal-β-HAla-β-HLeu-OMe) SEQ ID NO:2;

2 x) Methyl-N-{(tert-butoxy)carbonyl}-(R)-β-homovalyl-(S)-β-homoalanyl-(S)-β-homoleucyl-(2-amino-2-methylpropanoyl)-(R)-β-homovalyl-(S)-β-homoalanyl-(S)-β-homoleucinate (Boc-β-HVal-β-HAla-β-HLeu-Aib-β-HVal-β-HAla-β-HLeu-OMe) SEQ ID NO:1;

2 xi) Methyl-N-{(tert-butoxy)carbonyl}-(R)-β-homovalyl-(S)-β-homoalanyl-(S)-β-homoleucyl-(3-aminopropanoyl)-(R)-β-homovalyl-(S)-β-homoalanyl-(S)-β-homoleucinate (Boc-β-HVal-β-HAla-β-HLeu-β-HGly-β-HVal-β-HAla-β-HLeu-OMe) SEQ ID NO:4;

2 xii) Methyl-N-{(tert-butoxy)carbonyl}-(R)-β-homovalyl-(S)-β-homoalanyl-(S)-β-homoleucyl-(S)-β-homoalanyl-(R)-β-homovalyl-(S)-β-homoalanyl-(S)-β-homoleucinate (Boc-β-HVal-β-HAla-β-HLeu-β-HAla-β-HVal-β-HAla-β-HLeu-OMe) SEQ ID NO:5;

2 xiii) Methyl-N-{(tert-butoxy)carbonyl}-(R)-β-homovalyl-(S)-β-homoalanyl-(S)-β-homoleucyl-(2S,3S)-2-methyl-β-homoalanyl-(R)-β-homovalyl-(S)-β-homoalanyl-(S)-β-homoleucinate (Boc-β-HVal-β-HAla-β-HLeu-(S,S)-β-HAla(αMe)-β-HVal-β-HAla-β-HLeu-OMe) SEQ ID NO:5;

2 xiv) (R)-β-Homovalyl-(S)-β-homoalanyl-(S)-β-homoleucyl-(2S,3S)-2-methyl-β-homoalanyl-(R)-β-homovalyl-(S)-β-homoalanyl-(S)-β-homoleucine Trifluoroacetate (β-HVal-β-HAla-β-HLeu-(S,S)-β-HAla(αMe)-β-HVal-β-HAla-β-HLeu-OH.CF$_3$COOH) SEQ ID NO:5;

2 xv) Benzyl-(3S)-[N-{(tert-butoxy)carbonyl}-(R)-β-homovalyl-(S)-β-homoalanyl-(S)-β-homoleucyloxy]-butanoate (Boc-β-HVal-β-HAla-β-HLeu-(S)-3HB-OBn);

2 xvi) (3S)-[N-{(tert-butoxy)carbonyl}-(R)-β-homovalyl-(S)-β-homoalanyl-(S)-β-homoleucyloxy]-butanoic acid (Boc-β-HVal-β-HAla-β-HLeu-(S)-3HB-OH);

2 xvii) Methyl-N-{(tert-butoxy)carbonyl}-(R)-β-homovalyl-(S)-β-homoalanyl-(S)-β-homoleucyl-{(S)-3-hydroxy-butanoyl}-(R)-β-homovalyl-(S)-β-homoalanyl-(S)-β-homoleucinate (Boc-β-HVal-β-HAla-β-HLeu-(S)-3HB-β-HVal-β-HAla-β-HLeu-OMe) SEQ ID NO:1;

Also as described in publication No. 2. the following β-heptapeptides are synthesised for comparison purposes:

2 xviii) Methyl-N-{(tert-butoxy)carbonyl}-(R)-β-homovalyl-(S)-β-homoalanyl-(S)-β-homoleucyl-(R)-β-homoalanyl-(R)-β-homovalyl-(S)-β-homoalanyl-(S)-β-homoleucinate (Boc-β-HVal-β-HAla-β-HLeu-(R)-β-HAla-β-HVal-β-HAla-β-HLeu-OMe) SEQ ID NO:1;

2 xix) Methyl-N-{(tert-butoxy)carbonyl}-(R)-β-homovalyl-(S)-β-homoalanyl-(S)-β-homoleucyl-(3-amono-3- methylbutanoyl)-(R)-β-homovalyl-(S)-β-homoalanyl-(S)-β-homoleucinate (Boc-β-HVal-β-HAla-β-HLeu-β-HAib-β-HVal-β-HAla-β-HLeu-OMe) SEQ ID NO:1;

2 xx) Methyl-N-{(tert-butoxy)carbonyl}-(R)-β-homovalyl-(S)-β-homoalanyl-(S)-β-homoleucyl-(2R,3S)-2-methyl-β-homoalanyl-(R)-β-homovalyl-(S)-β-homoalanyl-(S)-β-homoleucinate (Boc-β-HVal-β-HAla-β-HLeu-(R,S)-β-HAla(αMe)-β-HVal-β-HAla-β-HLeu-OMe) SEQ ID NO:5;

2 xxi) Methyl-N-{(tert-butoxy)carbonyl}-(R)-βhomovalyl-(S)-β-homoalanyl-(S)-β-homoleucyl-(S)-N-methyl-β-homoalanyl-(R)-β-homovalyl-(S)-β-homoalanyl-(S)-β-homoleucinate (Boc-β-HVal-β-HAla-β-HLeu-Me-β-HAla-β-HVal-β-HAla-β-HLeu-OMe) SEQ ID NO:5;

These latter compounds have "non-allowed" β-amino acid residues (i.e. residues having substituents which are in the axial orientation) at their central positions and exhibit CD spectroscopy results which indicate an at least partial loss of secondary structure.

The above compounds are $\beta^3$ peptides, i.e. peptides having sidechains in the β position. The preparation of $\beta^2$ peptides of the invention, i.e. peptides having substuents in the α position, is described in the T. Hintermann and D. Seebach publication identified above as publication No. 3, and also as described in the examples below.

The abbreviations, procedures and equipment used in these examples are identified below. The synthesis and analysis procedures used are essentially as described in publications Nos. 1 and 2 above. EDC (1-[3-(dimethylamino)propyl]-3-ethylcarbodiimide hydrochloride), HOBt (1-hydroxy-1H-benzotriazole), h.v. (high vacuum, 0.01–0.1 Torr), NMM (N-methylmorpholine).

General: Flash chromatography (FC): $SiO_2$60 (0.04–0.063, Fluka). IR: Perkin Elmer 1600 FTIR, v in $cm^{-1}$. NMR Spectra: Bruker AMX 500, Gemini 300 or Gemini 200. δ in ppm rel. to $SiMe_4$ (=0 ppm), J in Hz; Carbon multiplicities were assigned by DEPT techniques. MS: VG Tribrid spectrometer (El), VG ZAB2-SEQ with 3nitrobenzyl alcohol (FAB, 3-NOBA).

EXAMPLE 1

Preparation of Benzyl (2R)-2-{(2R)-3-[(tert-Butoxy)carbonylamino]-2methylpropanoyl amino methyl}-4-methylpentanoate A solution of (2R)-3-(tert-butoxy)carbonylamino-2-methylpropanoate (0.81 g, 4.0 mmol) in THF (20 ml) was cooled under Ar to –15° and successively treated with NMM (0.46 ml, 4.2 mmol), isobutyl chloroformate (0.55 ml, 4.2 mmol) and, after stirring for 5 min, a precooled solution of benzyl (2R)-2-aminomethyl4methylpentanoate toluenesulfonate ((2),1.79 g, 4.4 mmol) and NMM (0.48 ml, 4.4 mmol) in DMF (10 ml). The mixture was allowed to warm to r.t. over a period of 2 h and stirring was continued for further 2 h. The solvent was removed under reduced pressure, the residue dissolved in AcOEt and washed with 10% aq. citric acid (3x), sat. aq. $K_2CO_3$ (3x), $H_2O$ and sat. aq. NaCl soln. The org. phase was dried ($MgSO_4$) and evaporated. Purification by FC (hexane/AcOEt 2:1) yielded The title compound (1.46 g, 87%): White solid.$^1$H-NMR (200 MHz, $CDCl_3$): 0.92 (d, J=5.5, 6H, $CH(CH_3)_2$); 1.05 (d, J=6.5, 3H, $CHRCH_3$); 1.23–1.40 (m,1H, $CH(CH_3)_2$); 1.44 (s, 9H, $C(CH_3)_3$); 1.52–1.77 (m, 2H, $CH_2CH(CH_3)_2$); 2.30–2.50 (m, 1H, COCHR); 2.68–2.85 (m, 1H, COCHR); 3.08–3.42 (m, 3H, 3 NCH); 3.45–3.60 (m, 1H, NCH); 5.04 (br.,1H, NHCOCHR); 5.16 (s, 2H, $CH_2Ph$); 5.90 (br.,1H, NHCOOtBu); 7.10–7.28 (m, 5H, H-arom.).

EXAMPLE 2

Preparation of Benzyl (2R)-2-~(2R)-2-{(2R)-2-[(tert-Butoxy)carbonylamino]methyl-3methyl butanoylamino}-2-methylpropanoylaminomethyl~-4-methylpentanoate The Boc-protected dipeptide Benzyl (2R)-2-{(2R)-3-[(tert-Butoxy)carbonylamino]-2-methylpropanoylamino methyl}-4-methylpentanoate (243 mg, 0.58 mmol) was dissolved in sat. HCl/dioxane (1 ml) and stirred for 2 h at r.t. The solvent was evaporated, the residue dried under h.v. and dissolved in THF (5 ml). The solution was successively treated with (2R)-2-(tert-butoxy)carbonylaminomethyl-3-methyl butanoate (148 mg, 0.64 mmol), NMM (0.20 ml,1.8 mmol) and HOBt (95 mg, 0.70 mmol), cooled to 0° and treated with EDC (123 mg, 0.64 mmol). The mixture-was stirred at 0° for 1 h, then at r.t. for 6 h, diluted with AcOEt and washed with 10% aq. citric acid (3x), sat. aq. $K_2CO_3$ (3x), $H_2O$ and sat. aq. NaCl soln. (2x). The org. phase was dried ($MgSO_4$) and evaporated. Purification by FC ($Et_2O$) yielded the title compound (231 mg, 74%): White solid. $^1$H-NMR (300 MHz, $CDCl_3$): 0.85–0.92 (m, 12H, 2 $CH(CH_3)_2$); 1.00 (d, J=4.5, 3H, $CHRCH_3$); 1.14–1.30 (m, 1H, $CH_2CH(CH_3)_2$); 1.38 (s, 9H, $C(CH_3)_3$); 1.49–1.62 (m, 2H, $CH_2CH(CH_3)_2$); 1.74–1.88 (m, 1$CHRCH(CH_3)_2$); 2.02–2.13 (m, 1H, COCHR); 2.35–2.50 (m, 1H, COCHR); 2.66–2.77 (m, 1H, COCHR); 3.10–3.54 (m, 6H, 3 $NCH_2$); 5.08 (d, J=12.3,1H, $CH_2Ph$); 5.11 (br., 1H, NHBoc); 5.13 (d, J=12.3, $CH_2Ph$); 6.32 (br., 1H, CONH); 6.46 (br., 1H, CONH); 7.25–7.40 (m, 5H, H-arom.). $^{13}$C-NMR (75 MHz, $CDCl_3$): 15.7; 20.1; 20.9; 22.3; 22.6; 26.0; 28.4; 28.7; 38.9; 40.5; 40.8; 41.0; 42.2: 43.8: 54.0; 66.7; 79.3; 128.5; 128.7; 128.9; 136.0; 156.4; 174.8; 175.5; 175.6.

EXAMPLE 3

Preparation of (2R)-2-{(2R)-2-{(2R)-2-[(tert-Butoxy)carbonylamino]methyl-3-methyl butanoylamino}-2-methylpropanoylaminomethyl}-4-methylpentanoate To a solution of the benzylester, Benzyl (2R)-2-{(2R)-2-{(2R)-2-[(tert-Butoxy)carbonyl amino]methyl-3-methylbutanoylamino}-2-methylpropanoylaminomethyl}4 methyl pentanoate (177 mg, 0.33 mmol) in EtOH/DMF (5 ml/2.5 ml) under Ar, was added 10% Pd/C (15 mg). The Ar atmosphere was replaced by $H_2$, the suspension stirred for 18 h at r.t., the catalyst removed by filtration over Celite, and the filtrate evaporated. The title free acid obtained (152 mg) was used without further purification.

EXAMPLE 4

Preparation of Benzyl N-[(tert-Butoxy)carbonyl]-(R)-aminomethylvalyl-(R)-aminomethylalanyl-(R) aminomethylleucyl-(R)-aminomethylvalyl-(R)-aminomethyl alanyl-(R)-aminomethyl leucinate The Boc-protected tripeptide, Benzyl (2R)-2-~(2R)-2-{(2R)-2-[(tert-Butoxy)carbonylamino]methyl-3methylbutanoylamino}-2-methylpropanoylaminomethyl~-4-methylpentanoate (107 mg, 0.20 mmol) was dissolved in sat. HCl/dioxane (1 ml) and stirred for 2 h at r.t. The solvent was evaporated, the residue dried under h.v. and dissolved in THF (8 ml). The acid, (2R)-2-{(2R)-2-~(2R)-2-[(tert-Butoxy)carbonylamino]methyl-3-methylbutanoylamino}-2-methyl propanoylaminomethyl}methylpentanoate (89 mg, 0.20 mmol) was added, the solution cooled to 0° and successively treated with NMM (0.067 ml, 0.60 mmol), HOBt (34 mg, 0.25 mmol) and EDC (42 mg, 0.22 mmol). The mixture was stirred at r.t. for 24 h, then diluted with $CHCl_3$ (75 ml) and washed with 10% aq. citric acid (3×), sat. aq. $K_2CO_3$ (3×), $H_2O$ and sat. aq. NaCl soln. (2×). The org. phase was dried ($MgSO_4$) and evaporated. Purification by FC ($CH_2Cl_2$/MeOH 19:1) yielded the title compound (119 mg, 69%): White solid. $[\alpha]D=-110.2$ (c=0.95, $CHCl_3$). IR ($CHCl_3$): 3445m, 3307m, 3008m, 2965s, 2873m, 1702m, 1654s, 1522s, 1469m, 1368m, 1170s. 1H-NMR (500 MHz, $CDCl_3$): 0.88–0.93 (m, 18H, 6 $CH_3$); 0.96 (d, J=6.6, 6H, 2 $CH_3$); 1.03 (d, J=7.0, 3H, $CH_3$); 1.16 (d, J=7.1, 3H, $CH_3$); 1.24–1.29 (m, 2H, 2 $CH_2CH(CH_3)_2$); 1.43 (s, 9H, $C(CH_3)_3$); 152–1.63 (m, 4H, 2 $CH_2CH(CH_3)_2$); 1.801.85 (m, 1H, $CHRCH(CH_3)_2$); 1.89–1.92 (m, 1H, $CHRCH(CH_3)_2$); 1.99–2.05 (m, 1H, COCHR); 2.06–2.11 (m, 1H, COCHR); 2.42–2.52 (m, 3H, 3 COCHR); 2.71–2.76 (m, 1H, COCHR); 3.05–3.75 (m, 12H, 6 $NCH_2$); 5.10 (d, J=12.3, 1H, $CH_2Ph$); 5.16 (d, J=12.2, 1H, $CH_2Ph$); 5.54 (t, J=5.9, 1H, NHBoc); 6.80 (br., 1H, NHCO); 7.02 (br., 1H, NHCO); 7.09 (br., 1H, NHCO); 7.15 (br., 1H, NHCO); 7.31–7.37 (m, 6H, 5 H-arom./NHCO). $^{13}$C-NMR (125 MHz, $CDCl_3$): 15.4; 15.5; 20.3; 20.4; 21.0; 21.1; 22.3; 22.6; 23.1 ($CH_3$); 25.9; 26.0; 28.4; 28.4 (CH); 28.5 (CH3); 38.8; 38.8; 39.8 ($CH_2$); 40.8 (CH); 41.0; 41.2 ($CH_2$); 42.0; 42.3; 42.6; 42.8; 44.3; 45.3; 54.8; 55.1 (CH); 66.7 ($CH_2$); 79.0 (C); 128.2; 128.3; 128.6 (CH); 135.9; 156.3; 174.6; 174.6; 174.9; 175.2; 175.3; 175.4 (C). MS (FAB): 860 (18, [M+1]+), 859 (30, M+), 764 (10), 761 (20), 760 (59), 759 (100), 91 (21).

EXAMPLE 5

Preparation of (R)-Aminomethylvalyl-(R)-aminomethylalanyl-(R)-aminomethylleucyl-(R)-aminomethylvalyl-(R)-aminomethylalanyl-(R)-aminomethylleucinate Trifluoroacetate

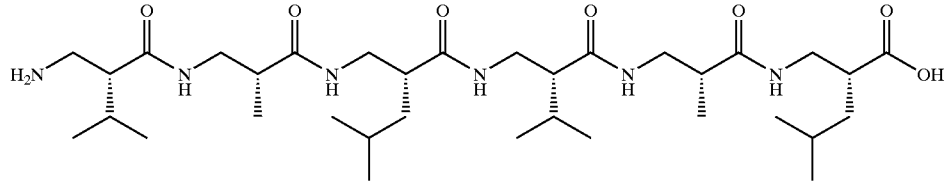

The Boc-protected hexapeptide, Benzyl N-[(tert-Butoxy)carbonyl]-(R)-Aminomethylvalyl-(R)-aminomethylalanyl-(R)-aminomethylleucyl-(R)--(R)-aminomethylvalyl-(R)-aminomethylalanyl-(R)-aminomethylleucinate (98 mg, 0.11 mmol) was dissolved in $CH_2Cl_2/CF_3COOH$ 1:1 (1 ml) and stirred for 4.5 h at r.t. The solvent was evaporated, the residue dried underh.v. and dissolved in MeOH (5 ml). To this solution 10% Pd/C (15 mg) was added underAr. The Ar atmosphere was replaced by $H_2$, the suspension stirred for 24 h at r.t, the catalyst removed by filtration over Celite, and the filtrate evaporated. The colorless oil obtained was purified by FC ($CH_2Cl_2$/MeOH 15:1), some $CF_3COOH$ was added, the solvent evaporated and the colorless oil dried underh.v. to give the title compound (83 mg, 96%): glass. $^1$H-NMR (300 MHz, $CD_3OD$): 0.85–1.03 (m, 24H, 4 $CH(CH_3)_2$; 1.09–1.16 (m, 6H, 2 $CHRCF_3$); 1.16–1.31 (m, 2H, 2 $CH_2CH(CH_3)_2$); 140–1.71 (m, 2H, 2 $CH_2CH(CH_3)_2$); 1.72–1.95 (m, 2H, 2 $CHRCH(CH_3)_2$); 2.22–2.32 (m, 1H, COCHR); 2.45–2.54 (m, 1H, COCHR); 2.55–2.84 (m, 4H, 4 COCHR); 3.06–3.43 (m, 1 OH, 10 NCH); 3.45–3.66 (m, 2H, 2 NCH). $^{13}$C-NMR (75 MHz, $CD_3OD$): 16.2; 16.7; 20.2; 20.8; 21.2; 22.6; 23.4; 23.7; 27.2; 27.4; 30.5; 30.9; 40.7; 40.7; 41.2; 41.8; 42.0; 42.6; 42.8; 43.5; 45.0; 45.7; 51.9; 54.1; 174.6; 176.1; 177.1; 177.6; 177.9; 179.0.

Compounds of formula I in which R and $R_3$ are both not H, i.e. $\alpha,\beta$ disubstuited compounds, may be prepared by alkylation of $Li_2$ derivatives generated from N-acyl-β-amino esters (D. Seebach, H. Estermann, Tetrahedron lett. (1987), 28, 3103 & D. Seebach, H. Estermann, Helv. Chim. Acta. (1988), 71, 1824).

Solid Phase Synthesis

The compounds of the invention may be synthesised using solid phase synthesis techniques.

Thus Fmoc-N-Protected β-amino acids of (S)-configuration bearing the side chains of Ala, Val, Leu and Phe in the 3- or 2-position are used to synthesise the β-heptapeptides H-β$^3$-HVal-β$^3$-HAla-β$^3$-HLeu-β$^3$-HPhe-β$^3$-HVal-β$^3$-HAla-β$^3$-HLeu-OH and H-β$^2$-HVal-β$^2$-HAla-β$^2$-HLeu-β$^2$HPhe-β$^2$-HVal-β$^2$-HAla-β$^2$-HLeu-OH by conventional manual solid-phase synthesis procedures under standard conditions on ortho-chloro-trityl chloride resin.

Esterification of Fmoc-β$^3$-HLeu-OH and Fmoc-β$^2$-HLeu-OH with the the ortho-chloro-trityl resin is performed according to the method of Barlos et al. (Tetrahedron Lett. (1989), 30, 3943). The resin (150 mg, 1.05 mmol Cl$^-$/g) is swelled in 2 ml $CH_2Cl_2$ for 10 min. A solution of Fmoc-β$^3$-HLeu-OH or Fmoc-β$^2$-HLeu-OH (41 mg, 112 μmol) in $CH_2Cl_2$ (2ml) and $iPr_2EtN$ (77 μl, 448 μmol) are then added successively and the suspension is mixed under Argon for 4 h. Subsequently, the resin is filtered and washed with $CH_2Cl_2$/MeOH/$ipr_2EtN$ (17:2:1, 3×3 min), $CH_2Cl_2$ (3×3 min), DMF (2×3 min), $CH_2Cl_2$ (3×3 min), MeOH (2×3 min). The substitution of the resin determined on a 3 mg sample by measuring the absorbance of the dibenzofulvene adduct at 300 nm, is 0.42 (74%) and 0.43 (75%) for Fmoc-β$^3$-HLeu-OH and Fmoc-β$^2$-HLeu-OH respectively. The Fmoc group is removed using 20% piperidine in DMF (4 ml, 2×20 min) under Ar bubbling. The resin is then filtered and washed with DMF (6×3 min). For each coupling step, a solution of the β$^2$- or β$^3$-amino acid (3 equiv.), BOP (3 equiv.) and HOBT (3 equiv.) in DMF (2 ml) and $iPr_2EtN$ (9 eq) are added successively to the resin and the suspension is mixed for 1 h under Ar. Monitoring of the coupling reaction is performed with 2,4,6-trinitrobenzene-sulphonic acid (TNBS) (W. S. Hancock and J. E. Battersby, Anal. Biochem. (1976), 71, 260) instead of the classical ninhydrin test (Fmoc deprotected β$^3$-peptide resin fails to give a blue colour with ninhydrin). In the case of a positive TNBS test (indicating incomplete coupling), the suspension is allowed to react for a further 1 h. The resin is then filtered and washed with DMF (3×3 min) prior to the following Fmoc deprotection step. After the removal of the last Fmoc protecting group, the resin is washed with DMF (6×3 min), $CH_2Cl_2$ (3×3 min), $Et_2O$ (3×3 min) and dried under h.v. for 3 h. Finally the peptides are cleaved from the resin using 2% TFA in $CH_2Cl_2$ (2 ml, 5×15 min) under Ar. The solvent is removed and the oily residues are triturated in ether to give the crude heptapeptides H-β$^3$-HVal-β$^3$-HAla-β$^3$-HLeu-β$^3$-

HPhe-β³-HVal-β³-HAla-β³-HLeu-OH (68 mg, 89%) and H-β²-HVal-β²-HAla-β²-HLeu-β²-HPhe-β²-HVal-β²-HAla-β²-HLeu-OH (60 mg, 79%) as white solids. The compounds are further purified by HPLC.

Peptides Comprising β²- and β³-Amino Acids

Peptides comprising a mixture of β²- and β³-amino acids are prepared essentially as described above for preparation of β²- and β³-peptides from appropriate β² and β³-amino acid starting materials. For example the following compounds are prepared:

3 i) (2S)-2-{(3S)-(3-tert-butoxycarbonylamino-butyrylamino)-methyl}-4-methyl-pentanoic acid benzylester; Smp: 113.0–113.5° C., $R_f$ (Pentane/EE 2:1)=0.25, $[\alpha]_D^{RT}=-23.0$ (c=0.85, $CHCl_3$)

3 ii) (3S)-3-(3-tert-butoxycarbonylamino-(2R)-2-methyl-propionylamino)-5-methyl-hexanoic acid benzylester; Smp: 113.5–114.0° C., $R_f$ (Pentane/EE 1:1)=4.5, $[\alpha]_D^{RT}=+7.9$ (c=0.97, $CHCl_3$)

3 iii) (2S2-({3-[(2S)-2-(tert-butoxycarbonylamino-methyl)-(3S)-3-methyl-butyrylamino]-butyrylamino}-methyl)-4methyl-pentanoic acid benzylester; Smp: 167.0–168.0° C., $R_f$ ($CH_2Cl_2$/MeOH 97:3)=0.30, $[\alpha]_D^{RT}=+10.6$ (c=0.95, $CHCl_3$)

3 iv) (3S)-3-[(3R)-3-(3-tert-butoxycarbonylamino4-methyl-pentanoylamino)-(2S)-2-methyl-propionylamino]-5-methyl-hexanoic acid benzylester; Smp: 126.0–127.0° C., $R_f$ ($CH_2Cl_2$/MeOH 97:3)=0.23, $[\alpha]_D^{RT}=+65.75$ (c=0.71, $CHCl_3$)

3 v) (3S)-3-(3-[3-[2-({3-[2-tert-butoxycarbonylamino-methyl)-3-methyl-(2S)butyrylamino]-(3S)-butyrylamino)-4-methyl-(2S)-pentanoylamino]-4-methyl-(3R)-pentanoylamino}-(2S)-2-methyl-propionylamino)-5-methyl-hexanoic acid benzylester; Smp: 209.0–210.0° C., $R_f$ ($CH_2Cl_2$/MeOH 96:4)=0.23, $[\alpha]_D^{RT}=+141.10$ (c=0.80, $CHCl_3$)

3 vi) (3S)-3-(3-[3-[2-({3-[2-aminomethyl-3-methyl-(2S) butyrylamino]-(3S)-butyrylamino)-4-methyl-(2S)-pentanoylamino]-4-methyl-(3R)-pentanoylamino}-(2S)-2-methyl-proionylamino)-5-methyl-hexanoic acid hydrochloride; characterised by NMR and MS(FAB) spectroscopy 3 vii) BocNHβ²-HVal-β³-HAla-β²-HLeu-β³ -HVal-β²-HAla-β³-HLeu-β²-HVal-β³-HAla-β²-HLeu-β³-HVal-β²-HAla-β³-HLeu-OBn; Smp: 220.0–221.0° C., $R_f$ ($CH_2Cl_2$/$Et_2O$/MeOH 48:48:4)=0.66, $[\alpha]_D^{RT}=+216.38$ (c=0.81, $CHCl_3$)

3 viii) TFA.H₂N-β²-HVal-β³-HAla-β²-HLeu-β³-HVal-β²-HAla-β³-HLeu-β²-HVal-β³-HAla-β²-HLeu-β³-HVal-β³-HAla-β²-HLeu-OH; characterised by NMR and MS(FAB) spectroscopy 3 ix) Benzyl (2R)-2-{(2R)-3-[(tert-butoxy)carbonylamino]-2-methylpropanoyl-amonomethyl}-4-methylpentanoate; $[\alpha]_D^{RT}=+53.3$ (c=1.07, $CHCl_3$)

3 x) (3S)-3-((3S)-3-tert-butoxycarbonylamino-butyrylamino)-5-methyl-hexanoicacidbezylester; Smp: 122.5–123.5° C., $R_f$ (Pentane/EE 3:1)=0.08, $[\alpha]_D^{RT}=-34.70$ (c=0.98, $CHCl_3$)

3 xi) Benzyl (2R)-2-{2R)-2-{(2R)-2-[(tert-butoxy)carbonylamnino]methyl-3-methyl-butanoylamino}-2-methylpropanoylaminomethyl}-4-methylpentanoate; $[\alpha]_D^{RT}=69.62$ (c=0.88, $CHCl_3$)

3 xii) (3S)-3-[(3R)-2-{(2R)-2-[(tert-butoxycarbonylamino-4-methyl-pentanoylamino)-(3S)-butyrylamino]-5-methyl-hexanoic acid benzylester; Smp: 178.5–179.5° C., $R_f$ ($CHCl_3$/MeOH 97:3)=0.37, $[\alpha]_D^{RT}=35.03$ (c=0.99, $CHCl_3$)

3 xiii) (3S)-3-(3-{3-[2-({3-[2-(tert-butoxycarbonylamino-methyl)-3-methyl-(2S)-butyrylamino]-2-methyl-(2S)-propionylamino}-methyl)-4-methyl-(2S)-pentanoylamino]4-methyl-(3R)-pentanoylamino}-(3S)-butyrylamino)-5-methyl-hexanoic acid benzylester; Smp: 221.0–222.0° C., $R_f$ ($CHCl_3$/$Et_2O$/MeOH 75:23:4)=0.12, $[\alpha]_D^{RT}=+88.98$ (c=0.57, $CHCl_3$)

3 xiv) (3S)-3-(3-{3-[2-({3-[2-aminomethyl-3-methyl-(2S)-butyrylamino]-2-methyl-(2S)-propionylamino}-methyl)-4-methyl-(2S)-pentanoylamino]-4-methyl-(3R)-pentanoylamino}-(3S)-butyrylamino)-5-methyl-hexanoic acid trifluoroacetate; characterised by NMR and MS (FAB) spectroscopy Struture Determinations, Results and Analysis Methods, analysis and results obtained for structural determinations for the compounds of the invention are described in detail in publications Nos. 1 and 2 above; including circular dichroism (CD) spectroscopy, NMR and X-ray crystallography determinations. These publications also include description of the methods used and results obtained in studies of the stability of the β-peptides of the invention to enzymatic degradation by pepsin.

Comparison of a Compound of Formula IV and a Compound of Formula V

The CD spectra and stability to enzymatic cleavage of the product [(R)-Aminomethylvalyl-(R)-aminomethylalanyl-(R)-aminomethylleucyl-(R)-aminomethylvalyl-(R)-aminomethylalanyl-(R)-(R)-aminomethylleucinate Trifluoroacetate] and the product [H-(β-HVal-β-HAla-β-HLeu)₂-OH-TFA] are compared.

Figure 1B:
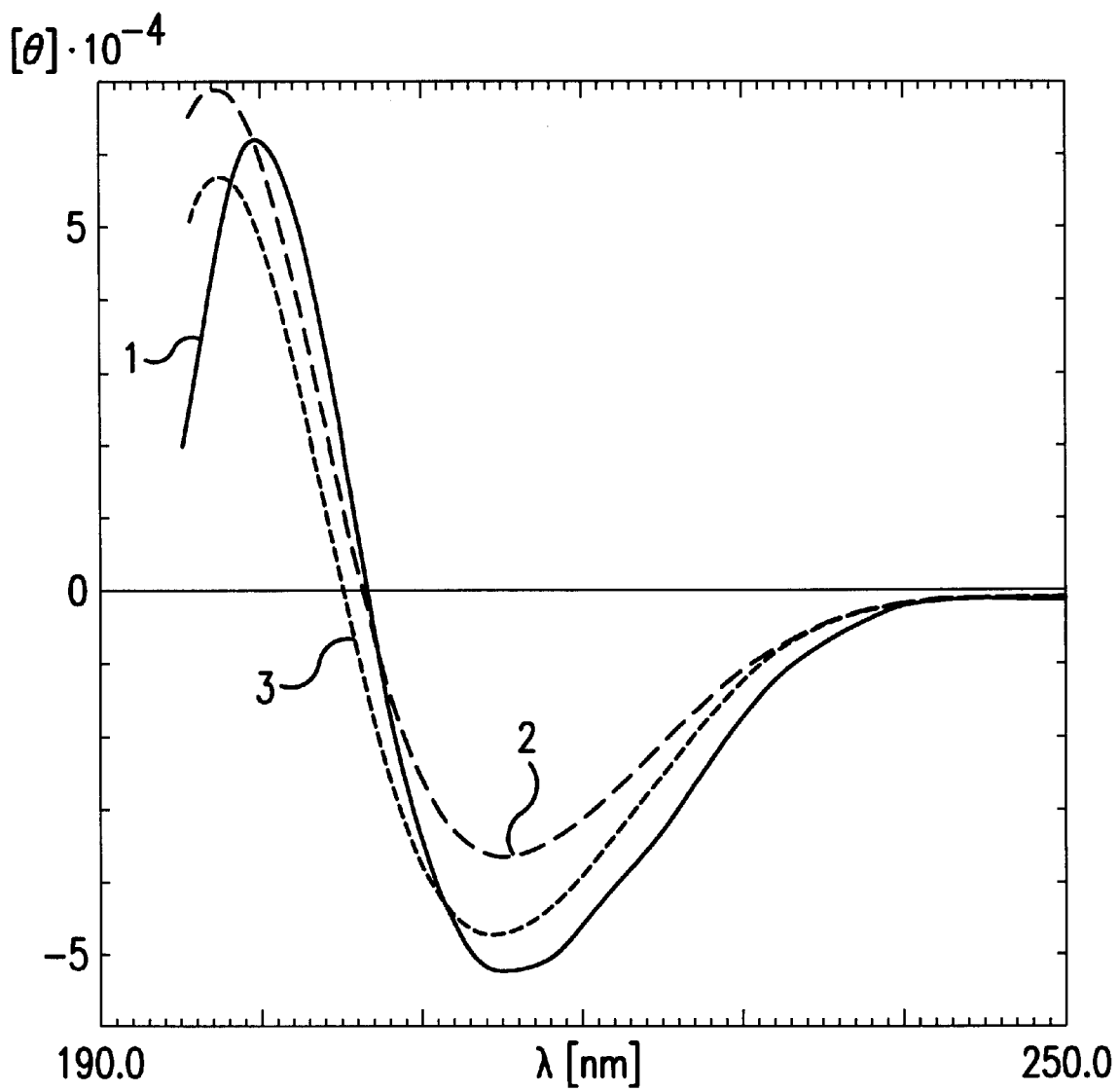
FIG. 1b is a CD spectra overlay of H-(β-HVal-β-HAla-β-HLeu)2-OMe SEQ ID NO:1 at 0.2 mM concentration in 1. MeOH, 2. trifluoroethanol (TFE) and 3. hexafluoro-2-propanol (HFIP)
Figure 1C:
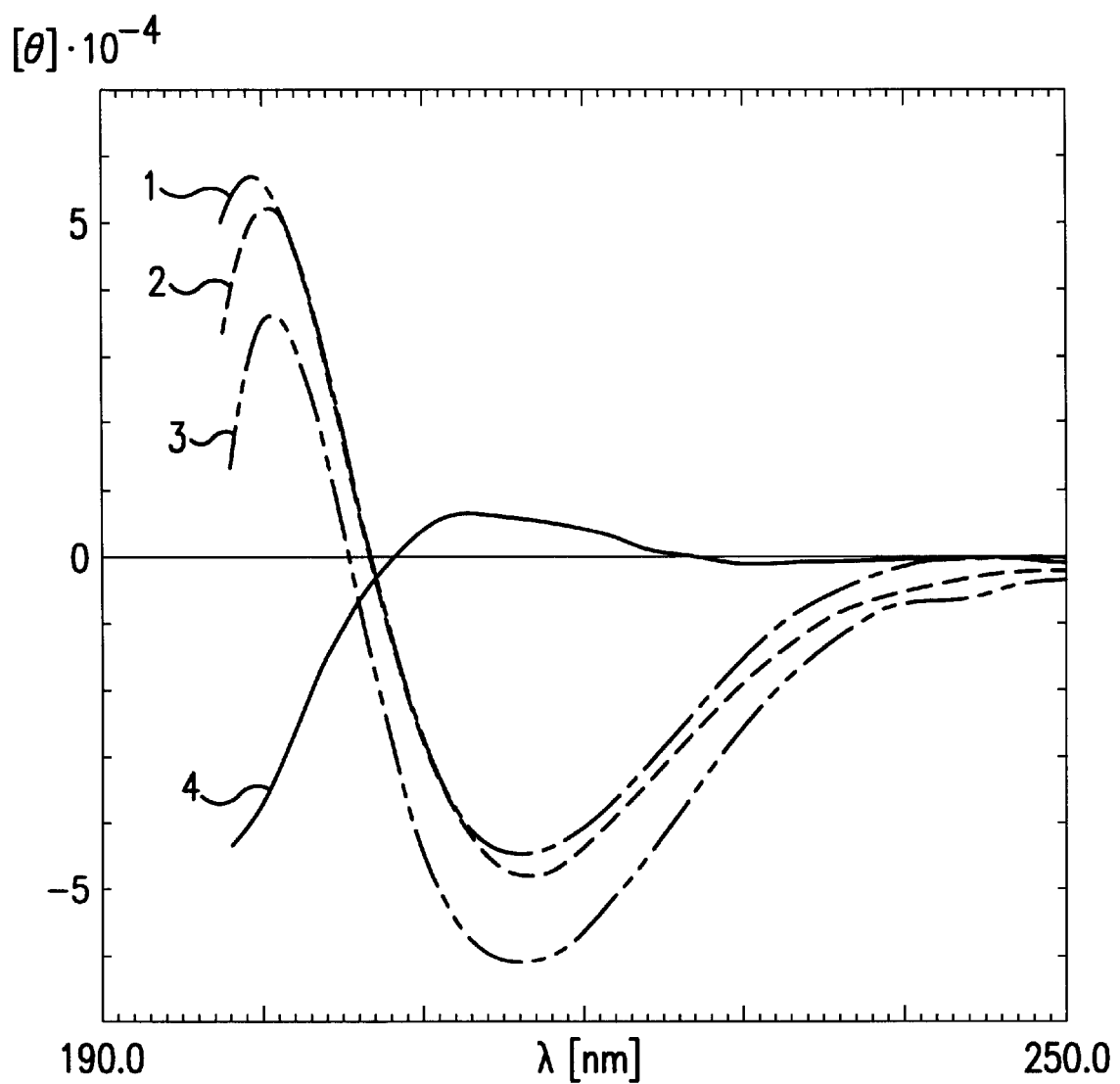
FIG. 1c is a CD spectra overlay of H-(β-HVal-β-HAla-β-HLeu)$_2$-OH.TFA SEQ ID NO:1 in MeOH at 1. 0.2 mM, 2. 0.04 mM and 3. 0.02 mM and 4. in Aqueous $H_2SO_4$ at pH<1.
Figure 1D:
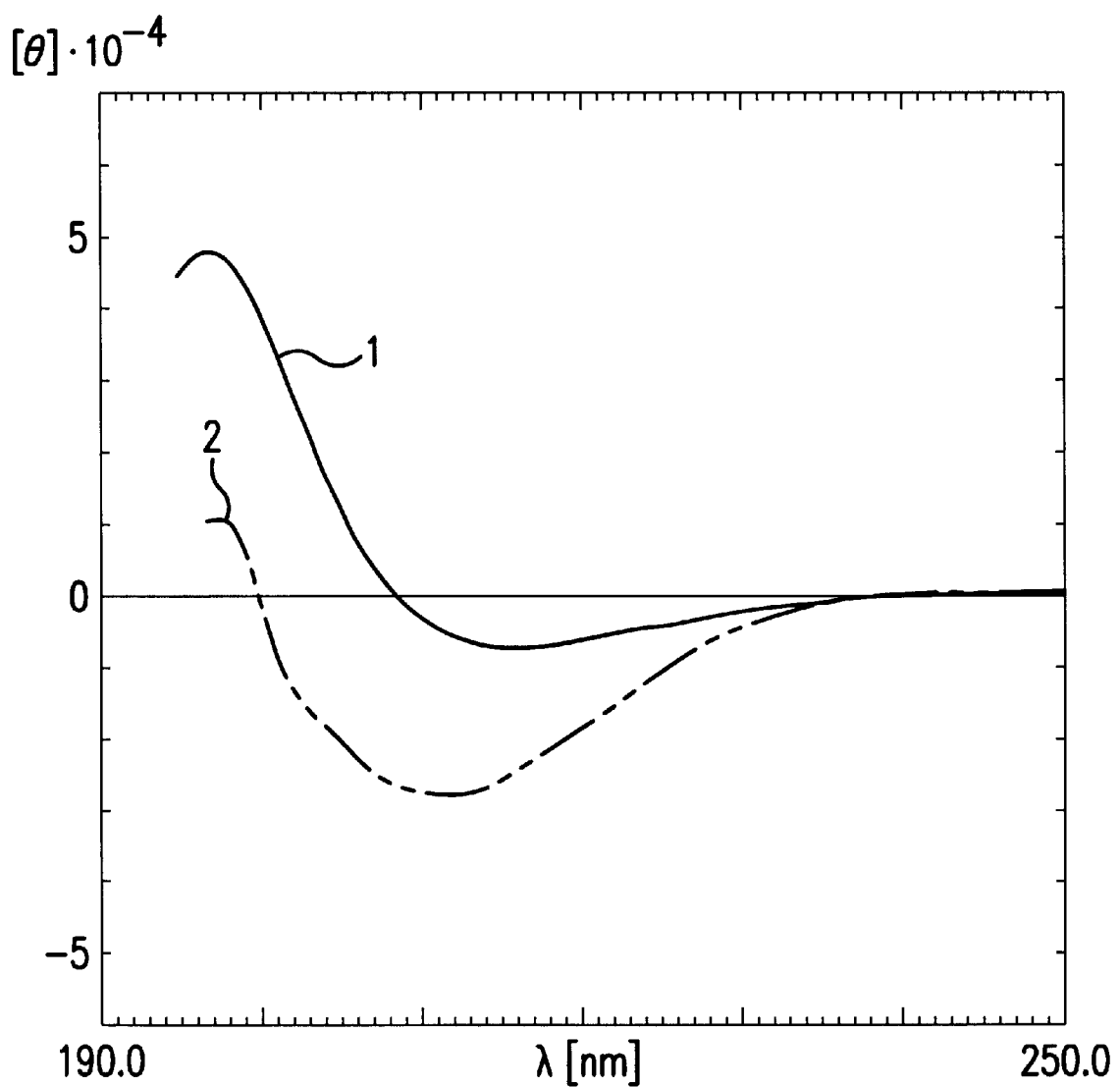
FIG. 1d is a CD spectra overlay of 1. the cyclic β-tripeptide cyclo(-β-HVal-β-HAla-β-HLeu-) in TFE and 2. the cyclic β-hexapeptide Cyclo(-β-HVal-β-HAla-β-HLeu-β-HVal-β-HAla-β-HLeu-) SEQ ID NO:1 at 0.2 mM concentration.
Figure 2B:
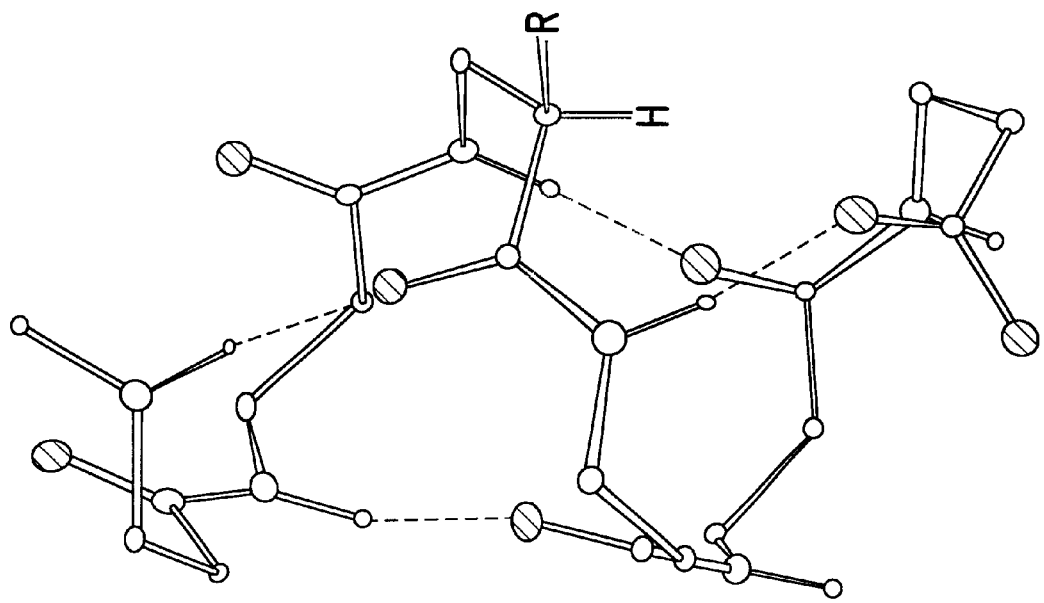
FIG. 2 shows a comparison of the $3_1$ helical structures of a) the left-handed helix of H-(β-HVal-β-HAla-β-HLeu)$_2$-OH.TFA SEQ ID NO:1 as determined by NMR spectroscopy and b) the predicted right-handed helical secondary structure of (R)-Aminomethylvalyl-(R)-aminomethylalanyl-(R)-aminomethylleucyl-(R)aminomethylvalyl-(R)-aminomethylalanyl-(R)-aminomethyl leucinate Trifluoroacetate, SEQ ID NO:1
Figure 2A:
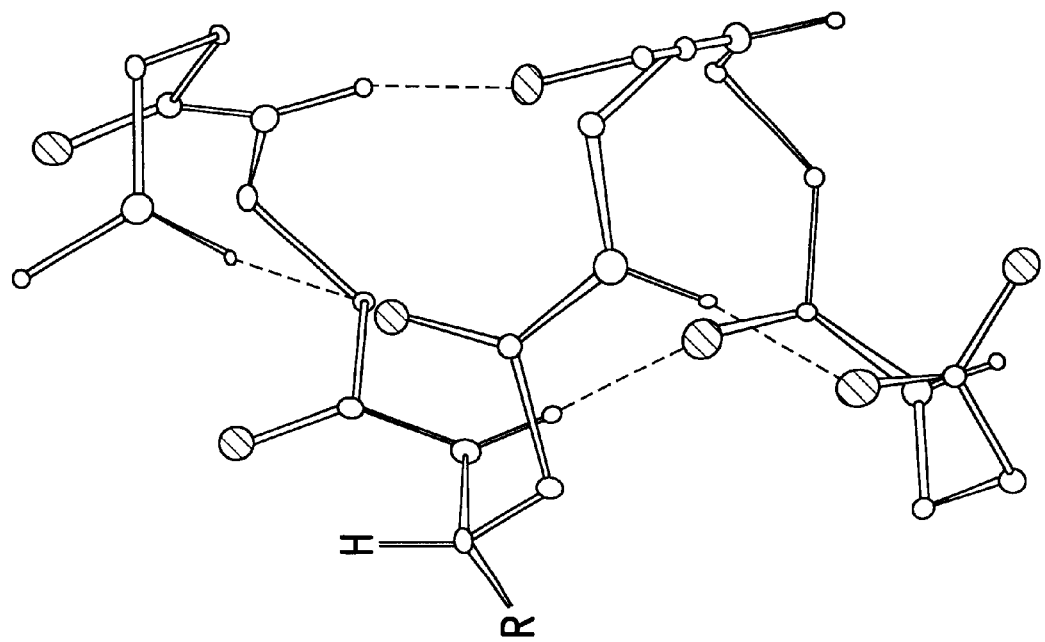
Figure 3:
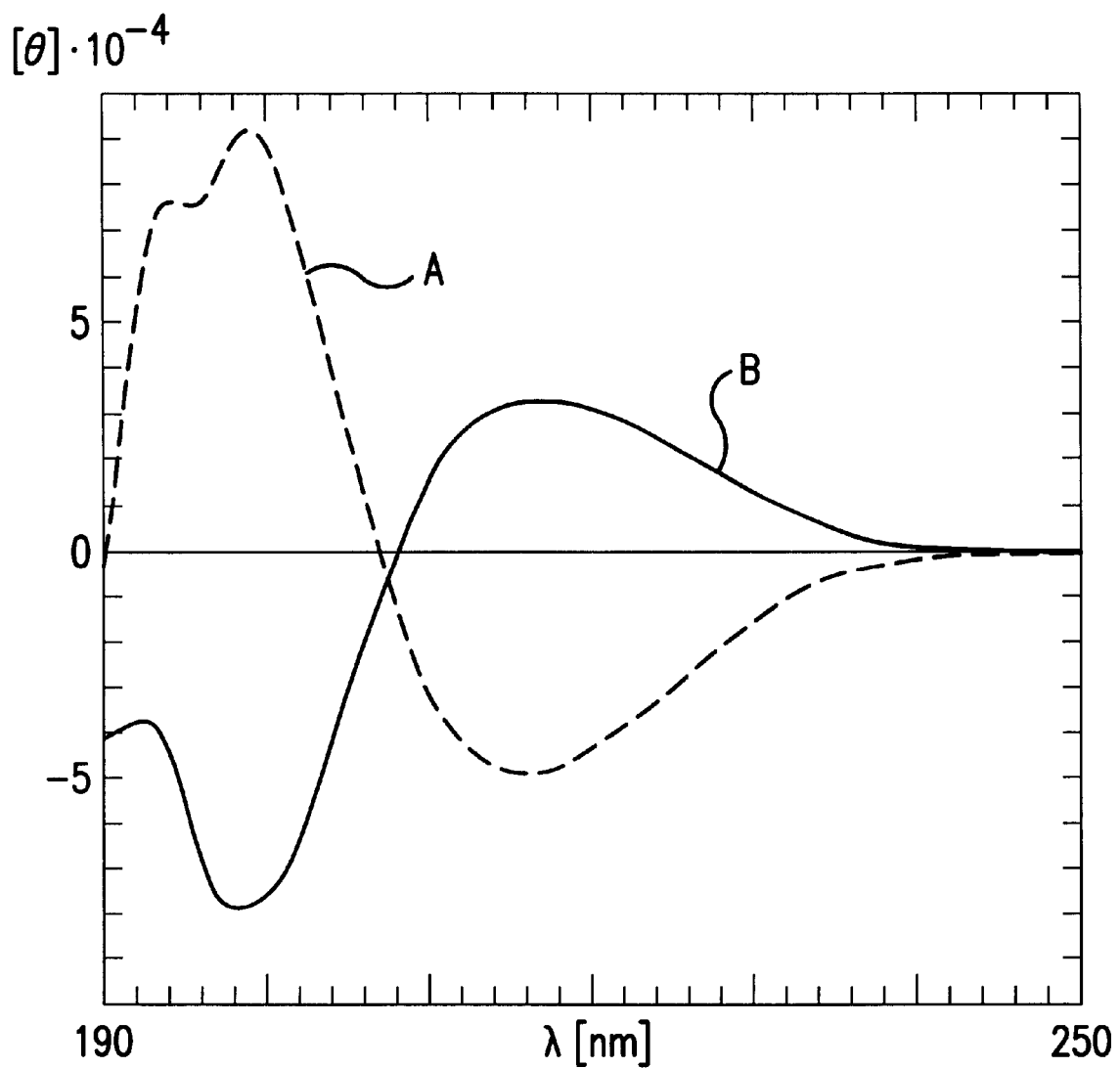
FIG. 3 is a CD spectra overlay of H-(β-HVal-β-HAla-β-HLeu)$_2$-OH.TFA SEQ ID NO:1 (curve A) and (R)-Aminomethylvalyl-(R)-aminomethylalanyl-(R)-aminomethylleucyl-(R)-aminomethylvalyl-(R)-aminomethylalanyl-(R)-aminomethyl leucinate Trifluoroacetate (curve B) in MeOH at a concentration of $2 \times 10^{-4}$, molar ellipeicity [Q] in 10 deg cm$^2$ Mol$^{-1}$.

As discussed in Seebach et al. publications Nos. 1 and 2 identified above, β-peptides such as H-(β-HVal-β-HAla-β-HLeu)₂-OH-TFA, built from L-configuration β-amino acids which are unsubstituted at the α-carbon atom, form (M) $3_1$ helices in MeOH solution (FIG. 2a). β-peptide built from β-amino acids which are unsubstituted at the β-carbon atom may be predicted to have the opposite (P) helicity as shown in FIG. 2b. As with α-peptides, the presence of a helical secondary structure of a β-peptide may be corroborated by optical measurements. As discussed in Seebach et al. publications Nos. 1 and 2 identified above, characteristic CD spectra have been observed for β-peptides such as H-(β-HVal-β-HAla-β-HLeu)₂-OH-TFA, with a typical pattern of a trough at ca. 216 and a peak at ca. 197 nm (see curve A in FIG. 3 and also FIGS. 1a to 1c). These characteristics are consistent with the (M) $3_1$ helical structure as shown in FIG. 3a. The CD spectrum in methanol of (R)-Aminomethylvalyl-(R)-aminomethylalanyl-(R)-aminomethylleucyl-(R)-aminomethylvalyl-(R)-aminomethylalanyl-(R)-(R)-aminomethyl leucinate Trifluoroacetate measured at room temperature is shown by curve B in FIG. 3. Indeed, the pattern of the spectrum of this latter compound is similar to that of H-(β-HVal-β-HAla-β-HLeu)₂-OH-TFA, but the sign of the cotton effect (CE) is positive at 216 nm (molar ellipticity Θ[10 deg cm² mol⁻¹]= 3.3×10⁴ vs −4.9×10⁴) and negative at 198 nm (Θ=−7.9×10⁴ vs 9.1×10⁴); such mirror image-type spectra result from the two isomers. This is consistent with (R)-Aminomethylvalyl-(R)-aminomethylalanyl-(R)-amino methylleucyl-(R)-aminomethylvalyl-(R)-aminomethylalanyl-(R)-aminomethylleucinate Trifluoroacetate forming a right-handed or (P) helix, the backbone of which has a mirror-image relationship with that of H-(β-HVal-β-HAla-β-HLeu)₂-OH-TFA (see FIG. 2). The less intense CE of the former compared to the latter may be indicative of a less stable structure. In order to examine the stability, the CD spectrum of the former is measured at −20° C. with the finding of a 40% increase in the molar ellipticity of the 216 nm CE. More dramatic alterations are found on change of solvents. Whereas the molar ellipticity at 216 nm decreases in water from $3.3 \times 10^4$ (methanol) to $1.7 \times 10^4$, it increases in acetonitrile to $5.9 \times 10^4$. Thus it appears that less polar solvents favour the formation of the secondary structure of (R)-Aminomethylvalyl-(R)-aminomethylalanyl-(R)-aminomethylleucyl-(R)-aminomethyl valyl-(R)-aminomethylalanyl-(R)-aminomethylleucinate Trifluoroacetate.

(R)-Aminomethylvalyl-(R)-aminomethylalanyl-(R)-aminomethylleucyl-(R)-aminoethylvalyl-(R)-aminomethylalanyl-(R)-(R)-aminomethylleucinate Trifluoroacetate is tested as a substrate for pepsin (as described for the $\beta^3$-peptides in Seebach et al. publications Nos. 1 and 2 identified above) and, as for the $\beta^3$-peptides, is found to be fully stable for several days under conditions for which the α-peptide H-(Val-Ala-Leu)$_2$-OH is degraded within minutes.

Peptides Comprising $\beta^2$- and $\beta^3$-Amino Acids

From structure determinations, peptides comprising alternate $\beta^2$- and $\beta^3$-amino acids, such as the hexapeptide identified above as compound 3 vi), appear to exhibit a stable structure, though this structure does not appear to be a $3_1$ helical structure. However, compounds stretches of $\beta^2$- and $\beta^3$-amino acids, such as the hexapeptide identified above a compound 3 xiv), do appear to exhibit $3_1$ helical structure.

Bioavailability

The oral bioavailability of a model β-peptide according to the invention, β-HAla-β-HLys-β-HAla-β-HLeu-β-HLys-β-HAla-β-HLeu, TFA salt is determined in the rat using standard procedures. The absolute oral bioavailabilty is found to be about 1%. It is to be expected that greater oral bioavailability may be seeen with other compounds of the invention, having substituents selected to improve this property.

The above compound is also administered intravenously to rats and found to have a relatively long terminal half life in blood of about 10 hours, with a systemic clearance of about 15 ml/min/kg and a volume of distribution of about 2 l/kg. It appears therefore that the relatively low oral bioavailability of the compound is due to low absorption from the gastrointestinal tract.

In view of the stable structures which β-peptides exhibit in solution, their stability to enzymatic degradation and their encouraging pharmacokinetic properties, the compounds of the invention have the potential to provide useful pharmaceutical products.

What is claimed is:

1. A compound of formula I

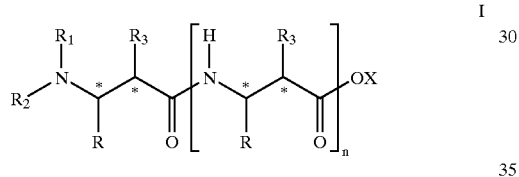

wherein each R is H, —$R_5$, —$OR_5$, —$C(O)R_5$, —$R_5C(O)R_6$, —$C(O)OR_5$, —$R_5C(O)OR_6$, —$R_5OC(O)R_6$, —$R_5OC(O)OR_6$, —$R_5NR_6C(O)R_7$, —$R_5C(O)NR_6R_7$, —$C(O)NR_6R_7$, —$R_6OC(O)NR_6R_7$, —$R_5NR_6C(O)NR_7R_8$, —$R_5NR_6C(O)OR_7$, —$R_5$—O—$R_6$, —$R_5$—$NR_6R_7$, —$R_5$—S—$R_6$, —$R_5$—$SO_m$—$R_6$, —$R_5OR_6$—O—$R_7$, —$R_5NR_6R_7$—O—$R_8$, —$R_5SO_mR_6$—O—$R_7$, —$C(O)R_5$—O—$R_6$, —$C(O)OR_5$—O—$R_6$, —$R_5C(O)R_6$—O—$R_7$, —$R_5C(O)OR_6$—O—$R_7$, —$R_5OC(O)R_6$—O—$R_7$, —$R_5OC(O)OR_6$—O—$R_7$, —$R_5NR_6C(O)R_7$—O—$R_8$, —$C(O)NR_5R_6$—O—$R_7$, —$R_5C(O)NR_6R_7$—O—$R_8$, —$R_5OC(O)NR_6R_7$—O—$R_8$, —$R_5NR_6C(O)NR_7R_8$—O—$R_9$, —$R_5NR_6C(O)OR_7$—O—$R_8$, —$R_5OR_6$—S—$R_7$, —$R_5NR_6R_7$—S—$R_8$, —$R_5SO_mR_6$—S—$R_7$, —$C(O)R_5$—S—$R_6$, —$C(O)OR_5$—S—$R_6$, —$R_5C(O)R_6$—S—$R_7$, —$R_5C(O)OR_6$—S—$R_7$, —$R_5OC(O)R_6$—S—$R_7$, —$R_5OC(O)OR_6$—S—$R_7$, —$R_5NR_6C(O)R_7$—S—$R_8$, —$C(O)NR_5R_6$—S—$R_7$, —$R_5C(O)NR_6R_7$—S—$R_8$, —$R_5OC(O)NR_6R_7$—S—$R_8$, —$R_5NR_6C(O)NR_7R_8$—S—$R_9$, —$R_5NR_6C(O)OR_7$—S—$R_8$, —$R_5OR_6$—$NR_7R_8$, —$R_5NR_6R_7$—$NR_8R_9$, —$R_5SO_mR_6$—$NR_7R_8$, —$C(O)R_5$—$NR_6R_8$, —$C(O)OR_5$—$NR_6R_8$, —$R_5C(O)R_6$—$NR_7R_8$, —$R_5C(O)OR_6$—$NR_7R_8$, —$R_5OC(O)R_6$—$NR_7R_8$, —$R_5OC(O)OR_6$—$NR_7R_8$, —$R_5NR_6C(O)R_7$—$NR_8R_9$, —$C(O)NR_5R_6$—$NR_7R_8$, —$R_5C(O)NR_6R_7$—$NR_8R_9$, —$R_5OC(O)NR_6R_7$—$NR_8R_9$, —$R_5NR_6C(O)NR_7R_8$—$NHR_9$, or —$R_5NR_6C(O)OR_7$—$NR_8R_9$, where $R_5$, $R_6$, $R_7$, $R_8$ and $R_9$ are each independently $C_{1-10}$alkyl, $C_{1-10}$alkenyl, $C_{1-10}$alkynyl, $C_{6-10}$aryl, $C_{6-14}$aralkyl, $C_{6-14}$aralkenyl or $C_{6-14}$aralkynyl and m is 1,2,3 or 4; and where $R_5$, $R_6$, $R_7$, $R_8$ and $R_9$ are each unsubstituted or substituted with up to 6 substituents selected from halo, $NO_2$, —OH, $C_{1-4}$alkyl, —SH, —$SO_3$, —$NH_2$, $C_{1-4}$acyl, $C_{1-4}$acyloxy, $C_{1-4}$alkylamino, $C_{1-4}$dialkylamino, trihalomethyl, —CN, $C_{1-4}$alkylthio, $C_{1-4}$alkylsulfinyl, or $C_{1-4}$alkylsulfonyl, provided that all the R substituents are not identical, or R forms a cyclic structure, with itself, with $R_3$ or with the carbonyl group attached to the immediately adjacent nitrogen atom;

X is hydrogen or an O-protecting group or as defined above for R, with the exception that X is not $OR_5$;

$R_1$ and $R_2$, which may be the same or different, are H, an N-protecting group or as defined above for R, or $R_1$ and $R_2$ are linked together in a 3 to 7 membered heterocyclic ring structure, or either $R_1$ or $R_2$ together with OX signify an amide bond to form a cyclic structure of formula

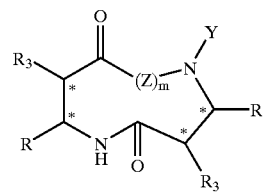

wherein Y is H, an amino protecting group or is as defined above for R, Z is —NH—CH(R)—CH($R_3$)—CO— and m is 1, 2, 3, 4, 5, 6, 7, 8 or 9;

each $R_3$, which may be the same or different, is as defined above for R, or $R_3$ forms a cyclic structure with the amino group which is alpha to the carbon bearing $R_3$, provided that R and $R_3$ are not both H; and n is 3, 4, 5, 6, 7, 8, 9, or 10.

2. A compound according to claim 1 in which n is 5 or 6.

3. A compound according to claim 1 of formula IV

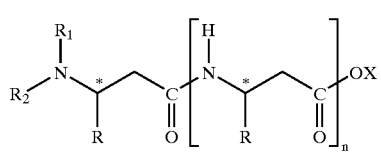

IV wherein R, $R_1$, $R_2$, X and n are as defined in claim 1.

4. A compound according to claim 1 which is a β-turn mimetic.

5. A composition comprising a compound according to claim 1 together with a pharmaceutically acceptable diluent or carrier.

6. A process for preparing a compound according to claim 1 comprising:
   (a) reacting a first β-amino acid for a time and under conditions effective to form a dipeptide in which an amide bond is present between the β-amino group of the first β-amino acid and the carboxyl group of the second β-amino acid;
   (b) reacting the peptide of step (a) with a further β-amino acid for a time and under conditions effective to form a peptide in which an amide bond is present between the terminal β-amino group of the peptide and the carboxyl group of the further β-amino acid;
   (c) optionally repeating step (b) 1, 2, 3, 4, 5 or 6 times; and
   (d) isolating the peptide of step (c).

7. A process for the preparation of a compound according to claim 1 comprising reacting an N-protected α-amino acid of formula VI

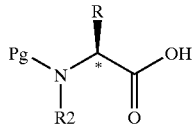

VI wherein Pg, is an amino protecting group and R and $R_2$ are as defined in claim 1, with diazomethane in the presence of triethylamine/ethylchloroformate to yield a diazo ketone intermediate of formula VII

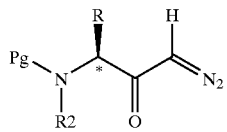

VII wherein Pg is an amine protecting group and R and $R_2$ are as defined in claim 1, coupling the compound of formula VII with a compound selected from a β-amino acid of formula VIII

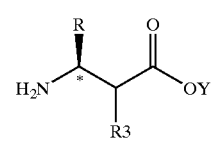

VIII wherein R and $R_3$ are as defined in claim 1 and Y is an O-protecting group or with a β-amino acid of formula IX

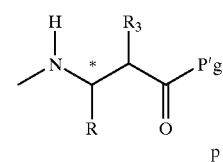

IX wherein R, $R_3$ are as defined in claim 1, P'g is an O-protecting group and p is 1, 2, 3, 4, 5, 6, 7, 8 or 9; and isolating the coupled compound.

8. A β-peptide comprising from 4 to 7 β-amino acid residues, wherein two or more amino acid residues are different.

* * * * *